(12) United States Patent
Bain et al.

(10) Patent No.: US 9,680,786 B2
(45) Date of Patent: Jun. 13, 2017

(54) COMMUNICATION AND NOTIFICATION SYSTEM AND METHOD THEREOF

(71) Applicant: Loop Communications, LLC, Colorado Springs, CO (US)

(72) Inventors: Kelly L. Bain, Colorado Springs, CO (US); James K. Dodd, Colorado Springs, CO (US)

(*) Notice: Subject to any disclaimer, the term of this patent is extended or adjusted under 35 U.S.C. 154(b) by 591 days.

(21) Appl. No.: 13/745,571

(22) Filed: Jan. 18, 2013

(65) Prior Publication Data

US 2013/0185369 A1 Jul. 18, 2013

Related U.S. Application Data

(60) Provisional application No. 61/587,938, filed on Jan. 18, 2012, provisional application No. 61/659,264, filed on Jun. 13, 2012.

(51) Int. Cl.
| | |
|---|---|
| G06F 15/16 | (2006.01) |
| H04L 12/58 | (2006.01) |
| H04L 29/08 | (2006.01) |
| G06Q 10/10 | (2012.01) |
| G06Q 50/22 | (2012.01) |

(52) U.S. Cl.
CPC .............. *H04L 51/24* (2013.01); *H04L 51/20* (2013.01); *G06Q 10/109* (2013.01); *G06Q 10/1095* (2013.01); *G06Q 50/22* (2013.01); *H04L 12/5885* (2013.01); *H04L 51/18* (2013.01); *H04L 51/34* (2013.01); *H04L 67/22* (2013.01)

(58) Field of Classification Search
CPC ......... H04L 51/18; H04L 51/24; H04L 51/34; H04L 12/5885; H04L 67/22; G06F 19/3456; G06F 19/3475; G06F 19/3481; G06F 19/3418; A61B 5/4833; G06Q 50/22; G06Q 10/109; G06Q 10/1095
USPC ....... 709/203, 206, 217, 219, 224, 230, 232, 709/238; 705/2, 3, 7.13, 7.15, 7.19, 7.21
See application file for complete search history.

(56) References Cited

U.S. PATENT DOCUMENTS

| | | | |
|---|---|---|---|
| 2004/0249672 A1* | 12/2004 | Bocionek et al. | 705/2 |
| 2007/0153993 A1* | 7/2007 | Cohen | 379/100.05 |
| 2008/0201174 A1* | 8/2008 | Ramasubramanian et al. | 705/3 |
| 2009/0144086 A1* | 6/2009 | Toleti et al. | 705/3 |
| 2009/0213852 A1* | 8/2009 | Krishnamurthi et al. | 370/389 |
| 2009/0281829 A1* | 11/2009 | Hansen et al. | 705/2 |
| 2011/0215933 A1* | 9/2011 | Darling et al. | 340/573.1 |
| 2011/0313784 A1* | 12/2011 | Harvey et al. | 705/2 |
| 2014/0316803 A1* | 10/2014 | Cohan et al. | 705/2 |

\* cited by examiner

*Primary Examiner* — Liangche A Wang
*Assistant Examiner* — Johnny Aguiar
(74) *Attorney, Agent, or Firm* — ASPIRE IP, LLC; Scott J. Hawranek

(57) ABSTRACT

The invention generally relates to a communication and notification system and method thereof, and more particularly to a method and system for providing, tracking, sending reminders, and receiving communications/notifications in response to end-users in a variety of commercial market segments, e.g., medical, governmental compliance and criminal.

18 Claims, 23 Drawing Sheets

US 9,680,786 B2

COMMUNICATION AND NOTIFICATION SYSTEM AND METHOD THEREOF

This application claims the benefit of Provisional Application Ser. Nos. 61/587,938 entitled "IMPROVEMENT TO DUI DATABASE", filed on Jan. 18, 2012, and 61/659,264 entitled "COMMUNICATION AND NOTIFICATION METHOD", filed on Jun. 13, 2012, all of which are hereby incorporated by reference in their entireties.

BACKGROUND OF THE INVENTION

Field of the Invention

The present invention generally relates to a communication and notification system and method thereof, and more particularly to a method and system for providing, tracking, sending and receiving reminders to end-users in a variety of commercial market segments, e.g., medical, governmental compliance and criminal.

Discussion of the Related Art

Past approaches to communication and notification systems were configured to provide notifications to an end user to perform a task or tasks. These approaches have included notification via computer, telephone or other methods. The problem with past approaches is they are open-ended systems and do not provide a mechanism for verification that the end user has received the notification and/or complied with the tasking required in the notification.

SUMMARY OF THE INVENTION

Accordingly, the invention is directed to a communication and notification system and method thereof that substantially obviates one or more of the problems due to limitations and disadvantages of the related art.

An advantage of the invention is to provide increased interactions between subscribers and the system.

Another advantage of the invention is to provide an automated system for individual and corporate social responsibilities and compliance.

Yet another advantage of the invention is a system configured to decrease medical expenses. The system may be effective at decreasing hospitalizations of users, reducing health insurance costs of subscribers, increasing drug and/or alcohol testing compliance of a user, increasing a user's independent living functionality, and other benefits.

Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the invention, as embodied and broadly described, an embodiment of the invention is directed towards a closed loop auto-escalation process to drive a user's behavior to interact and comply by employing a communication and notification system and method to allow a user to respond by notifications via a number of different communication techniques, e.g., text message, mobile phone, land line phone, email, social networking, tweets, or other future communication method.

In another aspect of the invention, the notification system can be integrated with an existing software system being used by drug and alcohol testing facilities. The notification system can be configured to locate a user and provide real-time guidance to a user, e.g., directions to treatment facilities within a predetermined radius of the user's current location.

In another aspect of the invention, the notification system may be configured with voluntary or involuntary functionality. Voluntary functionality allows a user to turn off communications or notifications from the system, while involuntary functionality does not allow a user to turn off communications or notifications from the system.

In another aspect of the invention, the system is implemented as Software as a Service and subscribed to by a user or subscriber and accessible over the network, e.g., internet.

In another aspect of the invention, a communication system for one of managing notifications and communications includes a computing device comprising at least one processor and at least one memory. The at least one processor and the at least one memory are communicatively arranged to perform any number of different functions including receiving and sending notification requests, retrieving user information including one or more user profiles, notification message information including one or more notifications, notification method information including one or more notification methods, and predetermined criteria to close a communication loop, sending a first notification based on the user information, the notification message information, the notification method information, and the predetermined criteria, wherein the first notification is sent with a first notification method, wherein the user and the system are at different locations, receiving a first response from the user in response to the first notification, and evaluating the first response to determine whether the response satisfies the predetermined criteria, when the predetermined criteria has been satisfied close the communication loop and record the first response, when the first response has not be been satisfied send a second notification based on the user information, the notification message information, the notification method information, and the predetermined criteria, wherein the second notification is sent with a second notification method. The system can be configured to iterate "N" number of times and multiple communication methods and message be open to the user or subscriber simultaneously.

Yet another aspect of the invention is directed towards a method for performing a notification service with a communication and notification system. The method includes retrieving user information including one or more user profiles, notification message information including one or more notifications, notification method information including one or more notification methods, and predetermined criteria to close a communication loop, sending a first notification based on the user information, the notification message information, the notification method information, and the predetermined criteria, wherein the first notification is sent with a first notification method, wherein the user and the system are at different locations, receiving a first response from the user in response to the first notification, and evaluating, with a processor, the first response to determine whether the response satisfies the predetermined criteria, when the predetermined criteria has been satisfied close the communication loop and record the first response, when the first response has not be been satisfied send a second notification based on the user information, the notification message information, the notification method information, and the predetermined criteria, wherein the second notification is sent with a second notification method.

Still yet another aspect of the invention is directed towards a computer-readable storage medium tangibly embodying a program of instructions executable by a machine wherein said program of instruction comprises a plurality of program codes for providing notifications and communications. The program of instruction including program code for retrieving user information including one or more user profiles, notification message information including one or more notifications, notification method information including one or more notification methods, and predetermined criteria to close a communication loop; program code for sending a first notification based on the user information, the notification message information, the notification method information, and the predetermined criteria, wherein the first notification is sent with a first notification method, wherein the user and the system are at different locations; program code sending a first notification based on the user information, the notification message information, the notification method information, and the predetermined criteria, wherein the first notification is sent with a first notification method, wherein the user and the system are at different locations; program code for receiving a first response from the user in response to the first notification; and program code for evaluating the first response to determine whether the response satisfies the predetermined criteria, when the predetermined criteria has been satisfied close the communication loop and record the first response, when the first response has not be been satisfied send a second notification based on the user information, the notification message information, the notification method information, and the predetermined criteria, wherein the second notification is sent with a second notification method; program code for waiting a predetermined duration for a second response; and program code for sending a third notification based on the user information, the notification message information, the notification method information, and the predetermined criteria, when the predetermined duration has elapsed, wherein the third notification is sent to a backup contact with a backup notification method, wherein the backup contact is not the user.

In another aspect of the invention, the system is configured to generate reports including compliance information on the messages, response information, and other useful information. For example, reports may include any such data points separating out any and all fields, fully customizable by either a subscriber or user to meet their needs. The reports may be configured to be automatically sent to one or more of a user, subscriber or third-party.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Figure 1:
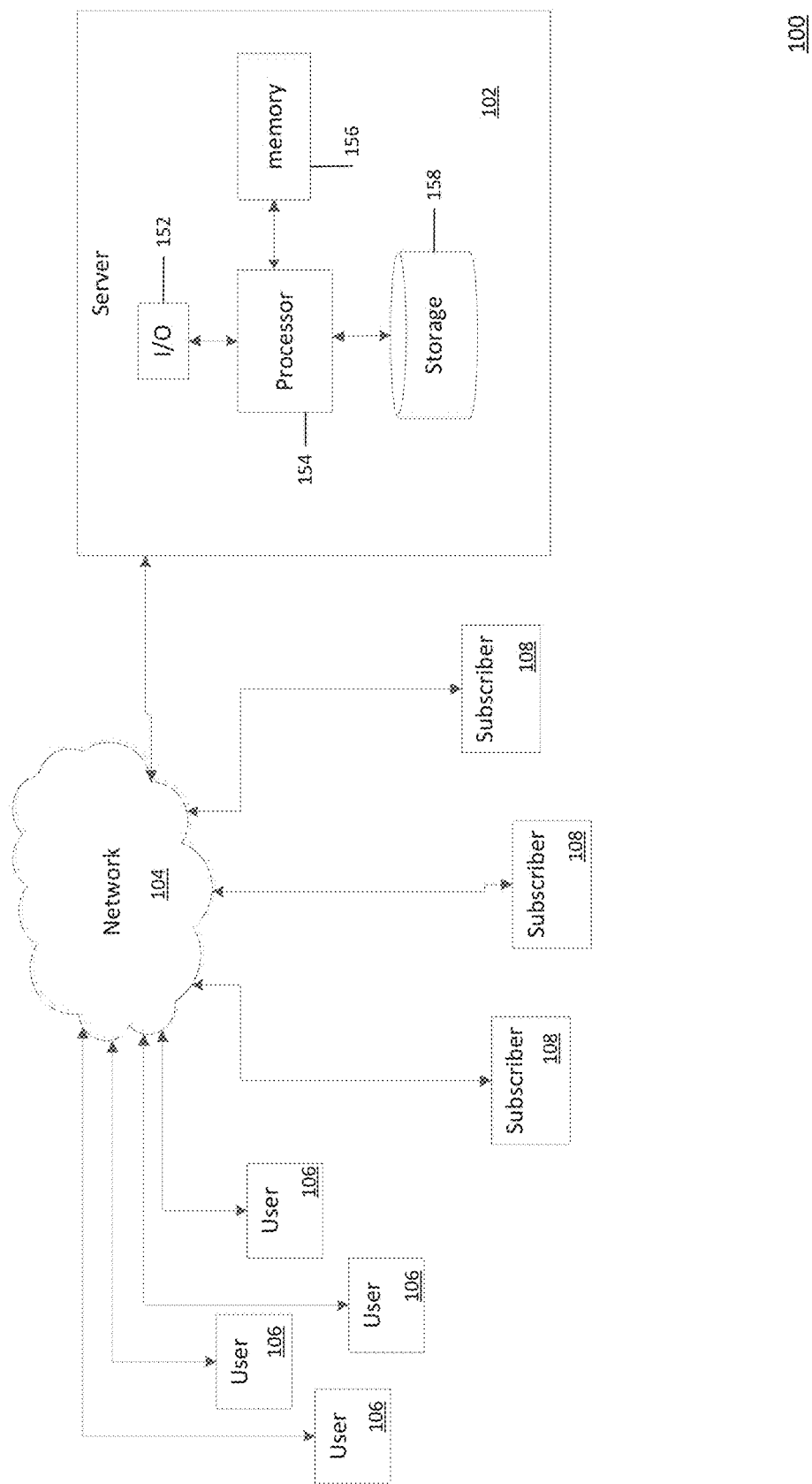
FIG. 1 is a block diagram of a communication and notification system according to an embodiment of the invention.

Appearances of the phrases an "embodiment," an "example," or similar language in this specification may, but do not necessarily, refer to the same embodiment, to different embodiments, or to one or more of the figures. The features, functions, and the like described herein are considered to be able to be combined in whole or in part one with another as the claims and/or art may direct, either directly or indirectly, implicitly or explicitly.

Functional units described in this specification may be labeled as modules, in order to more particularly emphasize their structural features. A module may be implemented as hardware, e.g., comprising circuits, gate arrays, off-the-shelf semiconductors such as logic chips, transistors, or other discrete components. They may be fabricated with Very-Large-Scale Integration (VLSI) techniques. A module may also be implemented in programmable hardware such as field programmable gate arrays, programmable array logic, programmable logic devices or the like. Modules may also be implemented in software for execution by various types of processors.

An identified module of programmable or executable code may, for instance, include one or more physical or logical blocks of computer instructions which may, for instance, be organized as an object, procedure, or function. Components of a module need not necessarily be physically located together but may include disparate instructions stored in different locations which, when joined logically together, include the module and achieve the stated function for the module. A module and/or a program of executable code may be a single instruction, or many instructions, and may even be distributed over several different code segments, among different programs, and across several memory devices. Similarly, data or input for the execution of such modules may be identified and illustrated herein as being an encoding of the modules, or being within modules, and may be embodied in any suitable form and organized within any suitable type of data structure.

In embodiments of the invention, the system, components and/or modules discussed herein may include one or more of the following: a server or other computing systems including a processor for processing digital data, a memory coupled to the processor for storing digital data, an input digitizer coupled to the processor for inputting digital data, an application program stored in one or more machine data memories and accessible by the processor for directing processing of digital data by the processor, a display device coupled to the processor and memory for displaying information derived from digital data processed by the processor, and a plurality of databases or data management systems.

Embodiments may be in terms of functional block components, screen shots, user interaction descriptions, optional selections, various processing steps, and the like. It should be appreciated that such descriptions may be realized by any number of hardware and/or software components configured to perform the functions described. Accordingly, to implement such descriptions, various integrated circuit components, e.g., memory elements, processing elements, logic elements, look-up tables, input-output devices, displays and the like may be used, which may carry out a variety of functions under the control of one or more microprocessors or other control devices.

In embodiments of the invention, software elements may be implemented with any programming, scripting language, and/or software development environment, e.g., Fortran, C, C++, C#, COBOL, Apache Tomcat, Spring Roo, Web Logic, Web Sphere, HTML, GML, assembler, PERL, Visual Basic, SQL Stored Procedures, AJAX, extensible markup language (XML), Flex, Flash, Java, .NET and the like. Moreover, the various algorithms in embodiments may be implemented with any combination of data structures, objects, processes, routines or other programming elements.

In embodiments of the invention, any number of conventional techniques for data transmission, signaling, data processing, network control, and the like as one skilled in the art will understand may be used. Further, detection or prevention of security issues using various techniques known in the art, e.g., encryption, may be also be used in embodiments of the invention. Additionally, many of the functional units and/or modules herein may be described as being "in communication" with other functional units and/or modules. Being "in communication" refers to any manner and/or way in which functional units and/or modules, such as, but not limited to, computers, laptop computers, PDAs, mobile devices, smart phones, tablets, pagers, modules, and other types of hardware and/or software may be in communication with each other. Some non-limiting examples include communicating, sending and/or receiving data and metadata via a network, a wireless network, software, instructions, circuitry, phone lines, Internet lines, fiber optic lines, satellite signals, electric signals, electrical and magnetic fields and/or pulses, and/or the like.

By way of example, communication among the users, subscribers and/or server in accordance with embodiments of the invention may be accomplished through any suitable communication channels, such as, for example, a telephone network, an extranet, an intranet, the Internet, cloud based communication, point of interaction devices (point of sale device, personal digital assistant, cellular phone, kiosk, and the like), online communications, off-line communications, wireless communications, RF communication, transponder communications, local area network (LAN), wide area network (WAN), networked or linked devices and/or the like. Moreover, although embodiments of the invention may be implemented with TCP/IP communications protocols, other communication techniques may also be implemented using IEEE protocols, IPX, Appletalk, IP-6, NetBIOS, OSI or any number of existing or future protocols. Specific information related to the protocols, standards, and application software utilized in connection with the Internet is generally known to those skilled in the art and, as such, need not be detailed herein.

In embodiments of invention, the system provides and/or receives a communication or notification via the communication system to an end user. The communication is typically sent over a network, e.g., a communication network. The network may utilize one or more of a plurality of wireless communication standards, protocols or wireless interfaces (including CDMA, WCDMA, TDMA, UMTS, GSM, GPRS, OFDMA, WiMAX, FLO TV, Mobile DTV, WLAN, and Bluetooth technologies), and may be provided across multiple wireless network service providers. The system may be used with any mobile communication device service (e.g., texting, voice calls, games, videos, Internet access, online books, etc.), SMS, MMS, email, mobile, land phone, tablet, smartphone, television, vibrotactile glove, voice carry over, video phone, pager, relay service, teletypewriter, or GPS.

Reference will now be made in detail to an embodiment of the present invention, an example of which is illustrated in the accompanying drawings.

FIG. 1 illustrates an exemplary block diagram depicting a communication and notification system according to an embodiment of the invention;

Referring to FIG. 1, the system 100 includes a server 102 in communication over a network 104 with one or more users 106 and one or more subscribers 108. The user 106 may include any type of end-user that a subscriber would like to monitor and/or send notifications to or receive notifications from. Moreover, the user 106 may also be a subscriber 108, e.g., the same entity or person.

In one embodiment, the user 106 may include a company or government employee where the company or government or the employee has monitoring requirements imposed by law, or configured to minimize risk for another reason. For example, the employee may be required to have random drug and alcohol testing for compliance with a government regulation, e.g., airline employee, military personnel. The user 106 may be a criminal or civil offender assigned by courts to undergo monitoring of some kind, e.g., drug and alcohol compliance. The user 106 may be a parent and/or juvenile, e.g., adults undergoing domestic relation disputes. The user 106 may be a medical patient in need of monitoring by their physician or insurance company, e.g., a diabetic that needs monitoring to ensure compliance with treatment, a pain patient that needs monitoring to ensure no abuse of pain medications, a physical therapy patient or other type of patient that needs monitoring to ensure efficacy of treatment.

The subscriber 108 may include any type of organization, client or customer that would like to monitor and/or send and/or receive notifications to an end-user 106. Moreover, the subscriber 108 may also be the user 106, e.g., same entity or person. In one embodiment, the subscriber 108 may include a company or government employer where the company or government has an employee that would like to be monitored.

Figure 2:
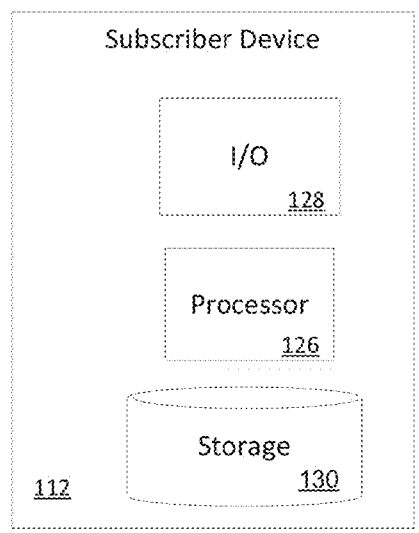
FIG. 2 is a block diagram of a subscriber device according to an embodiment of the invention.
Figure 3:
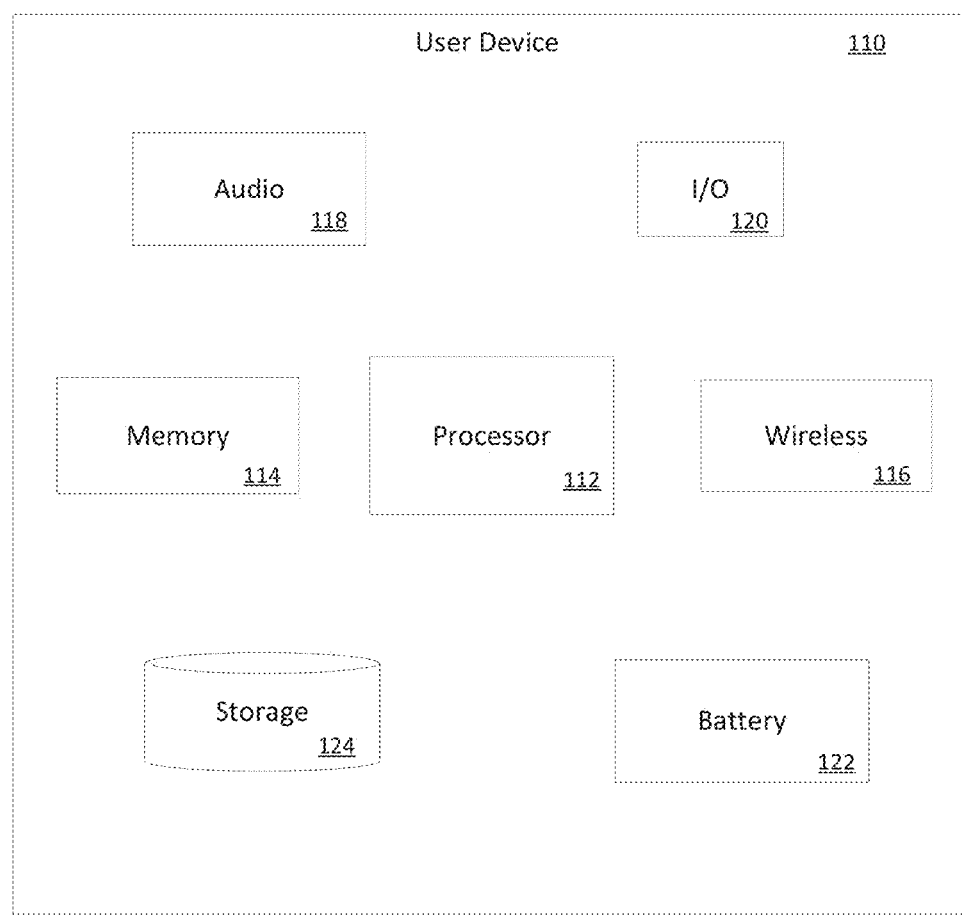
FIG. 3 is a block diagram of a user device according to an embodiment of the invention.

The server 102 is configured to send, receive, schedule, evaluate, program, and otherwise handle communication messages, alerts, and notification. The server 102 may also detect the identity and presence of one or more user 106. The server 102 may be configured to locate, e.g., wirelessly locate, the position of the one or more users 106 and/or subscribers 108 via user's device 110 and/or the subscriber's device 112 (FIGS. 2-3). The user device provides a user 104 with access to one or more of a plurality of data and/or communication services, also often called applications.

The user device 110 may include a mobile device, server, dummy terminal, land line phone, computer device or other future device to be created. In a preferred embodiment, the user device includes a mobile device 110 (as detailed below in FIG. 3). The device 110 is typically made operable by a subscriber contracting with a communication service provider (e.g., a wireless carrier) for obtaining wireless communication services. In this embodiment, the user is an individual person, a parent in a family, a business, or any person who wants the services offered to the mobile device 110. These types of users may also be an actual user of the mobile device 110, or the actual user may be a different person from the subscriber. For example, a parent may be a subscriber for providing communication services to the mobile device 110. Alternately, a business (the subscriber 108) may contract with a wireless carrier to provide communication services to a mobile device 110 for one of their employees who drives a company vehicle, as in a transportation vehicle like a bus, or a delivery vehicle, or another type of company-owned vehicle. In embodiments of the invention, location of the mobile device 110 may be accomplished via triangulation of signals between multiple cellular radio frequency towers, or other means available now or in the future known to one of ordinary skill in the art.

In FIG. 3, the mobile device 110 may be one of a laptop, iPad or other tablet computer, cell phone or another type of mobile communication device. In a preferred embodiment, the device 110 includes a processor 112, e.g., system-on-a-chip (SOC). The SOC may include an embedded microprocessor that combines a general purpose microprocessor core section with a collection of various peripheral cells to extend the PC architecture model into new applications that focus on low cost information and multimedia appliances. The SOC typically includes, in addition to a general purpose microprocessor core section, a memory controller, an I/O bus interface such as a PCI interface, a DMA controller and an interrupt controller (not shown). The SOC may be implemented with a commercially distributed component available from various semiconductor manufacturers. The SOC general purpose core section may be compatible with various microprocessor architectures.

The depicted embodiment of the SOC, in addition to including a suitable processor core cell, includes multiple peripheral cells designed to control various components of mobile computing device including a system memory 114 (DRAM, SRAM and/or the like), a wireless communication unit 116 suitable for transmitting and receiving wireless signals, and an audio unit 118 that is suitable for generating audio output and is suitable for playing files that are formatted in audio formats such as WAV, MIDI, and MP3.

The device 110 includes an I/O unit 120 including one or more I/O devices each configured to provide communication between a processor 112 and the outside world, possibly a user or another information processing system. The inputs may be accomplished with an input unit, e.g., a keyboard or a mouse and output may be accomplished with a monitor, printer or other output unit. However some I/O devices may serve for providing both inputs and outputs. There may be more than one I/O device in the I/O unit 120.

In a preferred embodiment, the device 110 includes a battery 122 that supplies power for the device 110 and additional storage 124, e.g., a non-volatile storage capacity in the form of a compact flash drive, cloud storage, hard drive and the like. The storage 124 may be of a size to hold operating system software to enable operation of the mobile device 110 or of larger or smaller size. Thus, the device 110 may be enabled to operate as a standalone unit for various applications including electronic scheduling and organizing, receiving and delivering email, internet browsing, form/fill transactions, and various other applications.

FIG. 2 is a block diagram of a subscriber device according to an embodiment of the invention. Referring to FIG. 2, the subscriber device 112 may include a mobile device, server, dummy terminal, land line phone, computer device or other future device to be created. In a preferred embodiment, the customer device includes a processor 126, I/O unit 128, and storage 130 as described herein with reference to FIG. 3. Moreover, the subscriber device 112 may include a mobile device as described with reference to FIG. 3.

The server 102 typically includes one or more of the following units communicatively coupled. An I/O unit 152, a processor 154, a memory 156, and additional storage 158. These units may be configured as and to operate as described herein with reference to FIG. 3.

Figure 4:
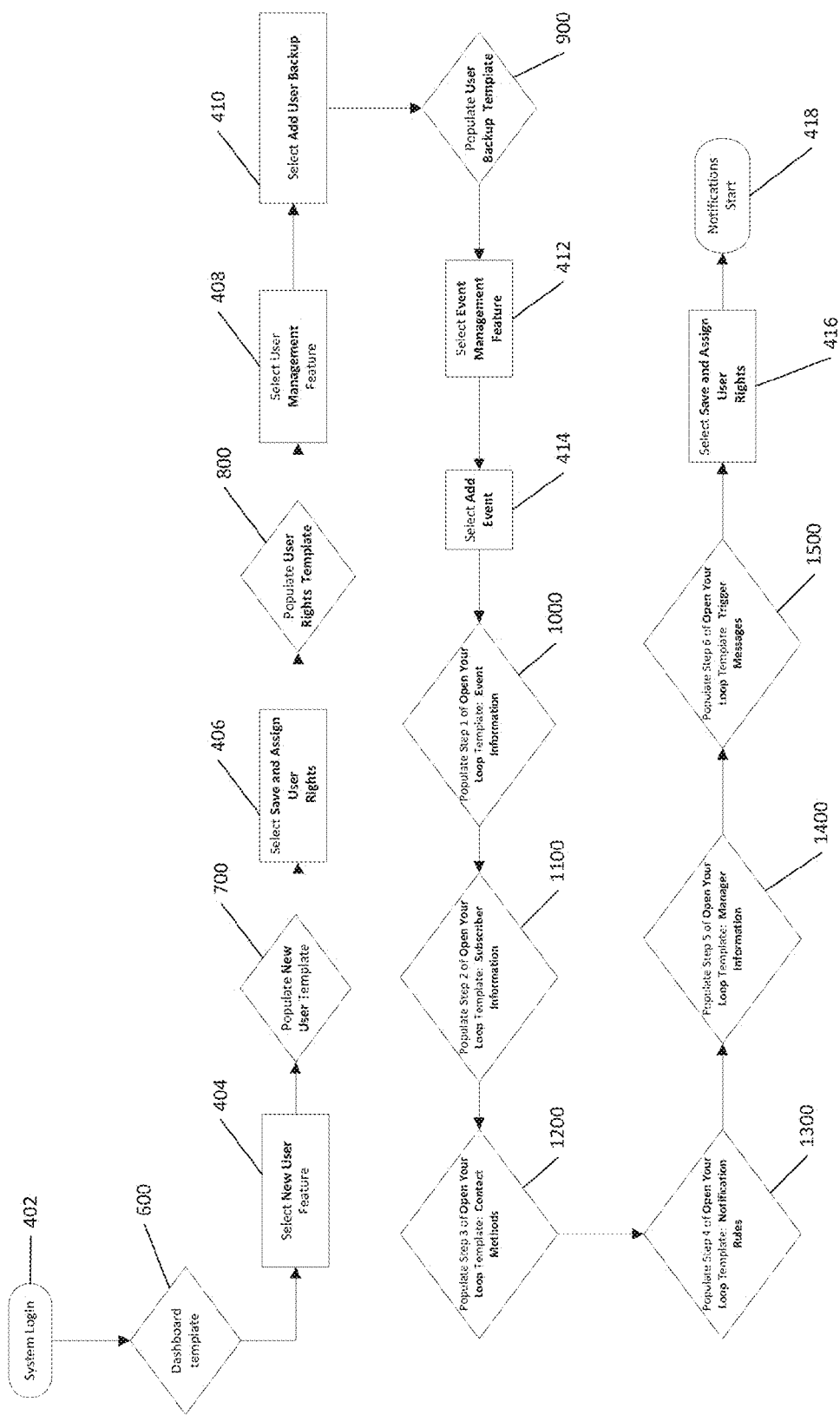
FIG. 4 is a block diagram of a user registration process according to an embodiment of the invention.

FIG. 4 is a block diagram of user registration process according to an embodiment of the invention.

Referring to FIG. 4, the registration process is generally depicted with reference to number 400. In various embodiments of the invention, the subscriber and user may be the same entity or person or a different entity or person. The configuration or registration process 400 of the system 100 sets the parameters for how the system 100 will monitor and/or send communications to one or more users 106 and/or subscribers 108.

In one embodiment, this registration process 400 entails having the subscriber configure the system with a predetermined hierarchy of communication or notification methods. This registration step may include assigning multiple notification methods, e.g., notification methods for each iteration of the notification and/or for each user. The notification methods of each iteration may be the same or different. By way of illustration the communication or notification method may include any one or more of voice, pager, text, video, picture, simple messaging system (SMS), email, multi-media messaging system, (MMS), TTY, television, radio frequency (RF), website messaging via HTML, JAVASCRIPT and other techniques, and any other to be developed communication methods.

Moreover, the notifications are configured to be sent at a predetermined time or dynamically sent over the network. The notification content is also customizable and may include a preconfigured media message, e.g., audio, video, picture, text and/or combinations of the same.

In this embodiment, the registration process is accomplished in an automatic progressive order as illustrated in FIG. 4. Moreover, in this embodiment, the subscriber registers the user. It is understood that the user may perform the registration step in any order and dynamically edit any information on the system.

Figure 5:
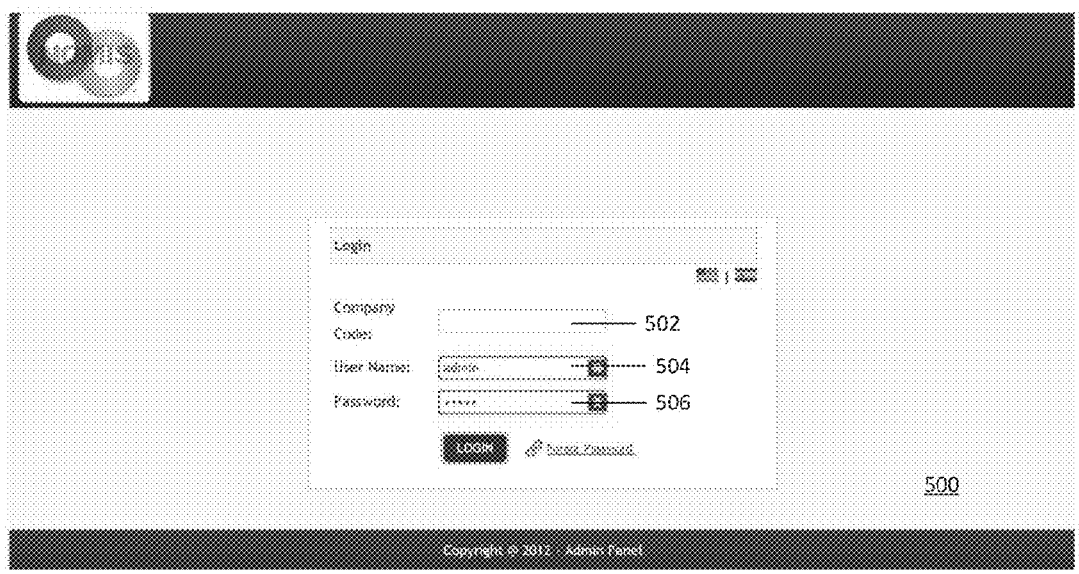
FIG. 5 is a screen shot of a login screen depicted in the process of FIG. 4.

Referring again to FIG. 4, a subscriber logs in to the system via a system login screen in step 402 to register a user. A screen shot of system login screen 500 is shown in FIG. 5 and has three data fields including a company code field 502, user name field 504 and password field 506. Access to the login screen 500 may be accomplished over the network 104 via the subscriber device 108 in step 402.

Figure 6:
FIG. 6 is a screen shot of a dashboard screen depicted in the process of FIG. 4.

After a successful login the user is directed towards a dashboard screen 600 shown in FIG. 6. The dashboard screen 600 is essentially a menu that includes a number of selectable options including, e.g., a new event 602, compliance report 604, manage subscriber 606, manage user 608, dashboard 610 (current screen), manage event 612, event notification report 614, new subscriber 616 and optionally others. In one embodiment, selecting the new event 602 will provide access to a new event 602 template allowing one to add the details of an event, selection of the compliance report 604 allows a user to generate various reports about the notifications and compliance, selecting the manage subscriber 606 allows a user to edit information on the subscriber, selecting the manage user 608 allows a user to edit information on the user, selecting the dashboard 610 returns the user to the current screen 600, selecting the manage event 612 allows a user to edit a preexisting event, selecting the event notification report 614 allows a user to prepare various reports on the notifications, and selecting the new subscriber 616 allows a user to add a new subscriber as described with reference to FIG. 7.

Figure 7:
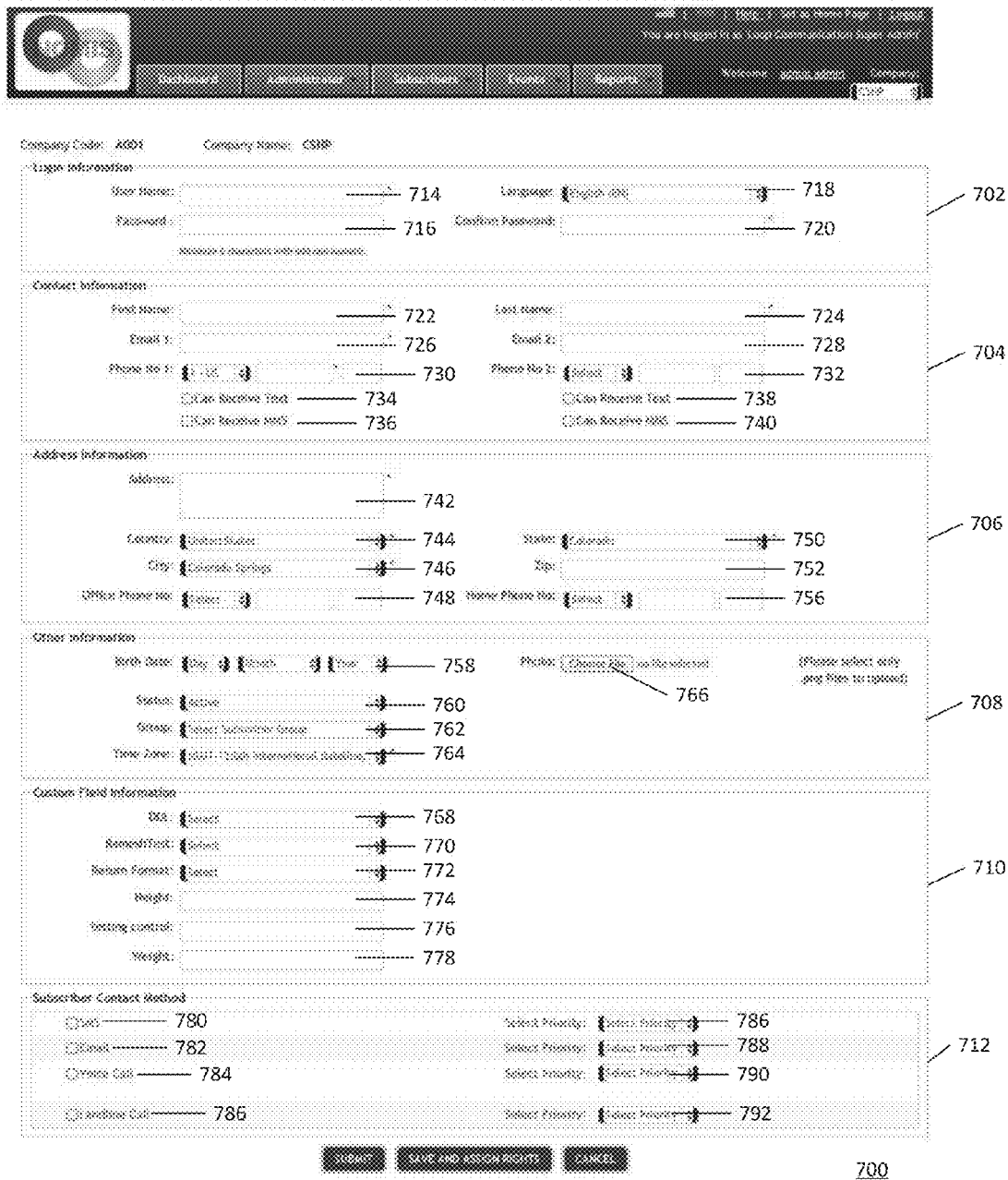
FIG. 7 is a screen shot of a new user/subscriber screen depicted in the process of FIG. 4.

In this embodiment, a new subscriber feature is selected in step 404 and a new user template 700 is sent to the subscriber device 112. A screen shot 700 of an illustrative example of the new user template is shown in FIG. 7. The new user template 700 includes a plurality of fields for receiving information about the user. In this embodiment, there are six high level organizational units each including selectable or fillable data fields including a login information unit 702, contact information unit 704, address information unit 706, other information unit 708, custom field information unit 710 and subscriber contact methods unit 712.

The login information unit 702 includes a plurality of selectable or fillable data fields, e.g., a user name field 714, a password field 716, language field 718 and confirmation of password field 720. The contact information unit 704 includes a plurality of selectable or fillable data fields including, e.g., a first name field 722, last name field 724, email-1 field 726, email-2 field 728, phone-1 field 730, specific information about the phone-1 field including whether phone-1 can receive text field 734 and whether phone-1 can receive MMS field 736, phone-2 field 732 and specific information about the phone-2 field 732 including whether phone-2 can receive text field 738 and whether phone-2 can receive MMS field 740.

The address information unit 706 includes a plurality of data fields including a physical street address 742, country 744, city 746, office phone 748, state 750, zip code 752, and home phone 756. The other information unit 708 includes a plurality of fields including birth date 758, status 760 either active or inactive, group 762 allows the user to be associated with a group, time zone 764, and photo 766 allows the user to upload one or more photos.

The custom field information unit 710 includes a plurality of fillable or selectable data fields such as drop down list (DDL) field 768. In one embodiment, the custom field information 710 allows for specific customization of data points that a company and/or user would like to add to their reports or compliance records. For example, there are no limitations on data one may utilize in a DDL field 768. All of the referenced fields fall under the customize company features. The ramesh test field 770, return format field 772, height field 774, testing control field 776 and weight field 778 are fields configured for a wellness program type scenario where a user/subscriber could track these fields, thereby tracking real-time progress with the wellness program. Again, any type of data may be tracked, utilized, monitored, and reported on in the custom field information unit 770.

Figure 8:
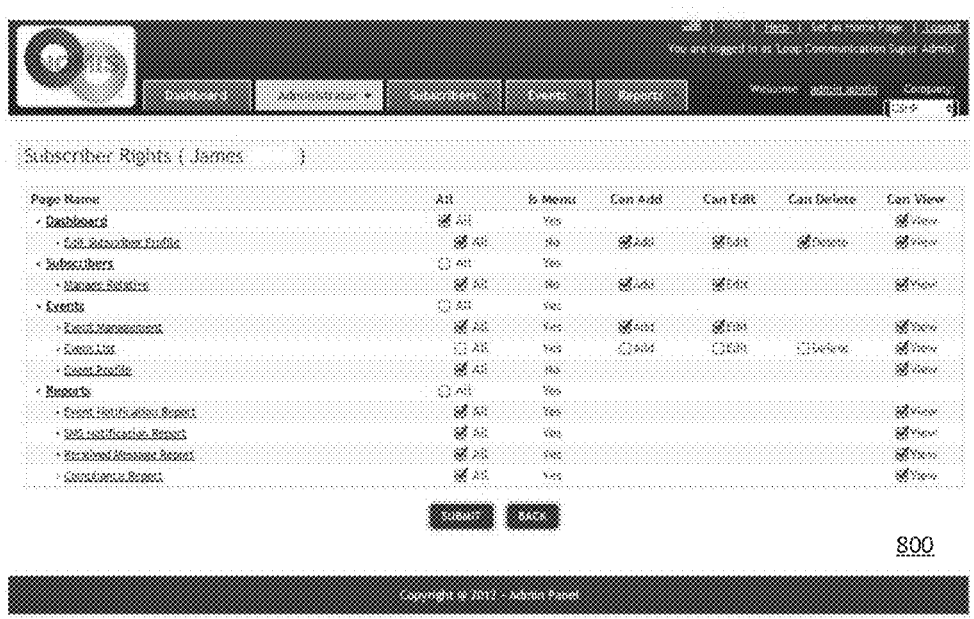
FIG. 8 is a screen shot of a user/subscriber rights screen depicted in the process of FIG. 4.

In step 406 the user selects and assigns the users rights thereby receiving the user rights template 800 shown in FIG. 8. The user rights template 800 includes a plurality of selectable or fillable data fields for assigning various rights for the user. The user configures the users rights or permissions within the system. In this embodiment, the user rights template 800 includes permission fields for dashboard, subscribers/users, events and reports. Moreover, not shown are further permission menus configured to provide the user with a plurality of rights within the system.

Figure 9:
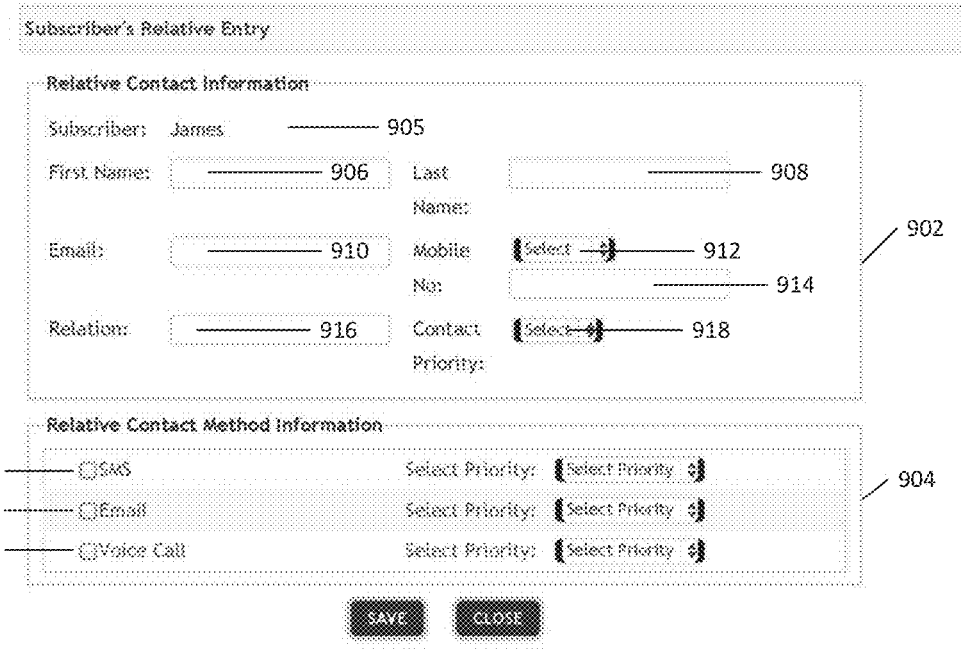
FIG. 9 is a screen shot of a user/subscriber backup screen depicted in the process of FIG. 4.

In step 408 the user selects the user management feature 408 and selects add user backup 410 from the dashboard 600, thereby receiving the user backup template 900 shown in FIG. 9. The user backup template 900 is utilized to configure contact methods and backup contacts. That is, the template is configured to specify the order to contact said 'relatives' in an emergency backup loop scenario with multiple levels and 'relatives' needed as necessary to infinity. The relative backup loop is opened separately to ensure the task being asked of the original receiver of the notification event is completed, assisting in closing their loop. A relative contact or backup contact used here interchangeably does not necessarily mean 'relative' it could be a co-worker or someone who works closely with the subscribed end user. In one embodiment, a big brother is watching with reports being sent to all concerned parties. Thereby, providing checks and balances humanistic approach to communication methods and/or messages still with accountability features built in addition to electronics that are not solely dependent on the electronic devices or methods.

In this embodiment, the user backup template 900 includes two high level organizational units each including selectable or fillable data fields including a relative contact information unit 902 and relative contact method information unit 904. The relative contact information unit 902 includes a plurality of fillable or selectable data fields including, e.g., subscriber field 905, first name field 906, last name field 908, email field 910, mobile number field 912, 914, relation field 916, and a contact priority field 918 which includes a plurality of selectable fields in which the 'relative' is positioned & the priority level order to be contacted. The relative contact method information unit 904 includes a plurality of fillable or selectable fields including a SMS field 920 which allows for a priority selection of 1-3, an email field 922 which allows for a priority selection of 1-3, and a voice call field 924 which allows for a priority selection of 1-3.

Figure 10:
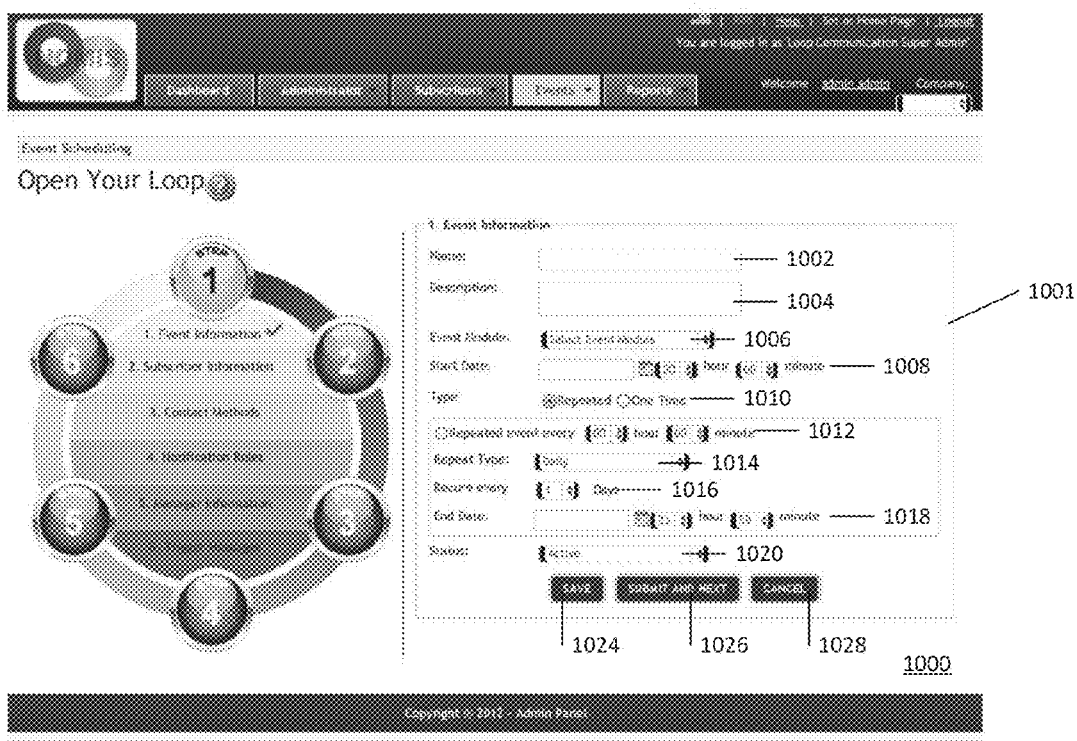
FIG. 10 is a screen shot of an notification/event information screen depicted in the process of FIG. 4.

In step 412 a user selects an event management feature 412 from the dashboard 600 and selects add an event in step 414. A screen shot of event information screen 1000 is shown in FIG. 10 and includes a plurality of fillable or enterable data fields. The event information template 1000 includes a name field 1002 where name of the event may be entered, a description field 1004 where a brief description of the event may be entered, and an event module field 1006 where a previously stored module with previous data may be selected. For example, the event module field 1006 is a module, depending on the industry, that will permit access to specific modules if a specific license has been purchased. That is, each module within the event module is pre-programed with automatic message templates for the particular industry and/or they may be further tailored. All of this area is fully customizable and is not limited to any one industry, instead encompasses all.

The event information screen further includes a start date/time field 1008 where a date and time of the event may be selected, a type field 1010 where the event is specified as either a one-time event or repeating event, repeated event field 1012 where an hour/minute can be selected to repeat the event, a repeat type field 1014 where the repeat duration of the start event is selected, e.g., daily, weekly, monthly, yearly, and the like, a recur every field 1016 where the repeating of the event is selected, e.g., daily, weekly, and the like, an end date field 1018 where the end of the event can be selected, and a status field 1020 where the status of the event can be either active or inactive. The user can save with the save 1024 command to save event information on the server 102, select the submit and next command 1026 to save the event information on the server 102 and move to the next step, or select a cancel command 1028 to cancel this step and return to the dashboard 600.

Figure 11:
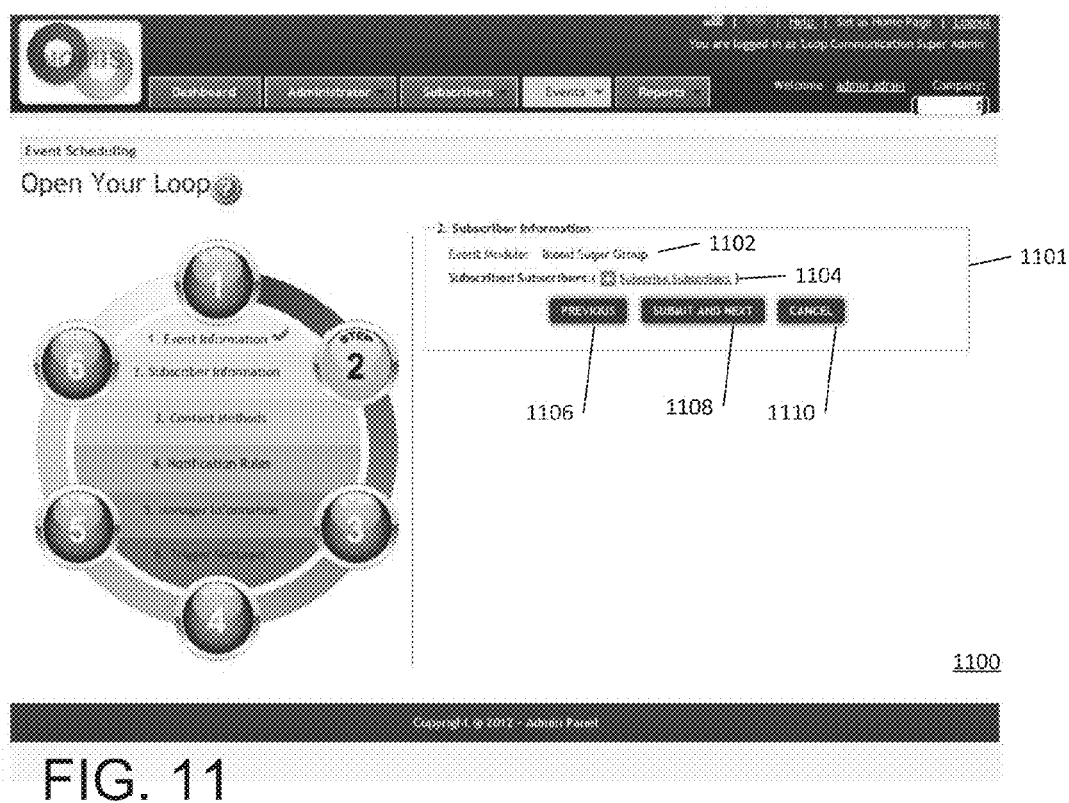
FIG. 11 is a screen shot of a user/subscriber information screen depicted in the process of FIG. 4.

After the user selects the submit and next command 1026 a subscriber information template 1100 is received on the user device. The subscriber information screen shot 1100 is shown in FIG. 11. The subscriber information screen includes a plurality of selectable or fillable data fields. In this step a user can select a list of subscribers 1104 for an event of the previous step the event module 1102. Multiple subscribers may be added to the same event module. The user can select a previous command 1106 command to return to the previous screen 1000, select the submit and next command 1108 to save the subscriber information on the server 102 and move to the next step, or select the cancel command 1110 to cancel this step and return to the dashboard 600.

Figure 12:
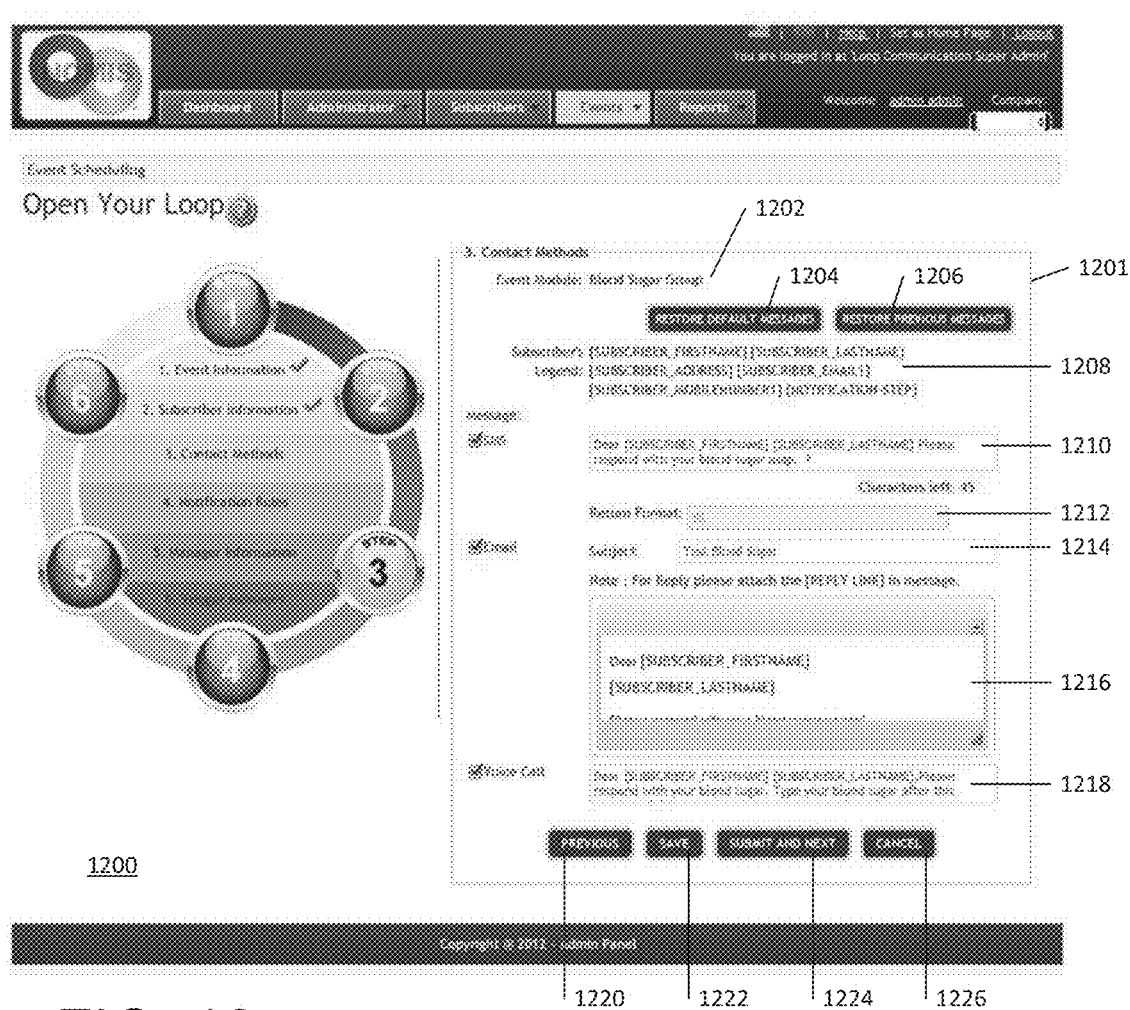
FIG. 12 is a screen shot of a contact methods screen depicted in the process of FIG. 4.

After the user selects the submit and next command 1108 a contact information template 1200 is received on the user device. The contact information screen shot 1200 is shown in FIG. 12. The contact information screen 1200 includes a plurality of selectable or fillable data fields. In this step a user can assign the notification methods and corresponding notification messages from a list of notification methods and messages for each event module. In addition, there is the ability to customize the notification to the personality of the subscribed end user receiving the message, e.g., the style of message most preferred for that user including but not limited to formal, informal, funny, rude, etc. There may also be an auto populated template of sample messages based on the specific module, however, all may be further customized or changed.

Referring to FIG. 12, the event module 1202 allows the user to select an event group to assign contact methods. The notification messages may also be previously stored as a default message or messages previously used and loaded with the restore default messages command 1204 or restore previous messages command 1206, respectively. The subscriber's legend field 1208 is configured to allow a user to merge fields listed in the message field 1210. That is, in the message field 1210 a user can create a customized notification message to be sent to a user utilizing message codes. For example, one illustrative message may include "Dear [[subscriber/user]] please respond with your blood sugar test results as soon as possible." Moreover, field 1210 is associated with an SMS notification method. A return format field 1212 is also associated with the SMS notification method, which allows a user to specify applicable return formats from the SMS response.

The email notification field 1214 is a subject line for the notification message sent via email and notification field 1216 is a body of the message. The voice call notification field 1218 includes the body of the message to be utilized as text for hearing impaired, text-to-voice or both. Other notification message modules may also be used, e.g., pictures, video and the like.

The user can select a previous command 1220 command to return to the previous screen 1100, select a save command 1222 to save the contact methods on the server 102, select the submit and next command 1224 to save the subscriber information on the server 102 and move to the next step, or select the cancel command 1224 to cancel this step and return to the dashboard 600.

After the user selects the submit and next command 1224 a notification rules template 1300 is received on the user device. The notification template 1300 includes a notification rules module 1302 having a plurality of selectable or fillable data fields for assigning specific rules for handling the notification messages and receipt of responses to notification messages. In this embodiment, the notification rules module 1302 includes a resend notification before response module 1308, reply after response from subscriber module 1310, response information module 1312 and resend notification if not delivered module 1314.

Figure 13:
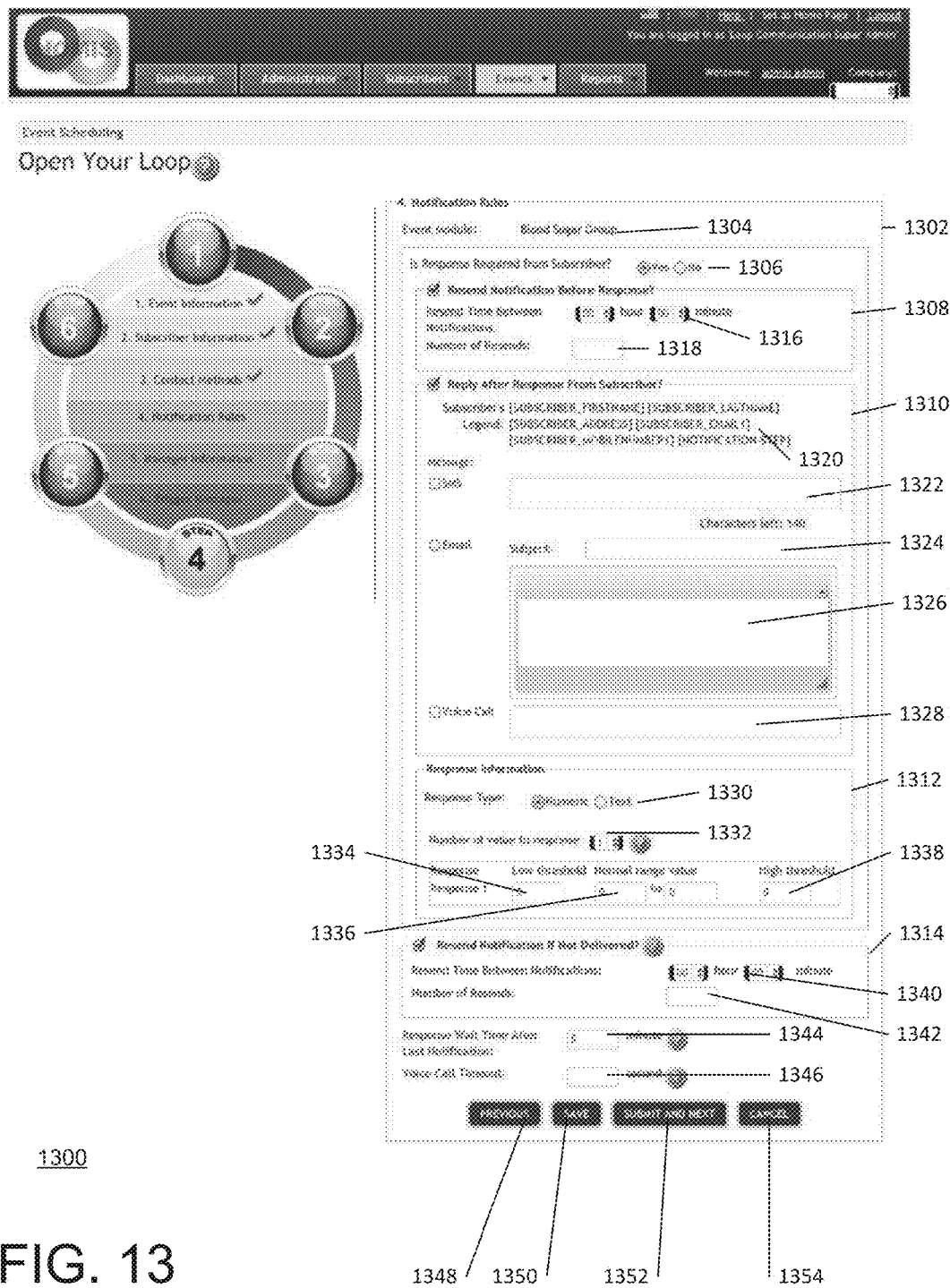
FIG. 13 is a screen shot of a notification rules screen depicted in the process of FIG. 4.
Figure 14:
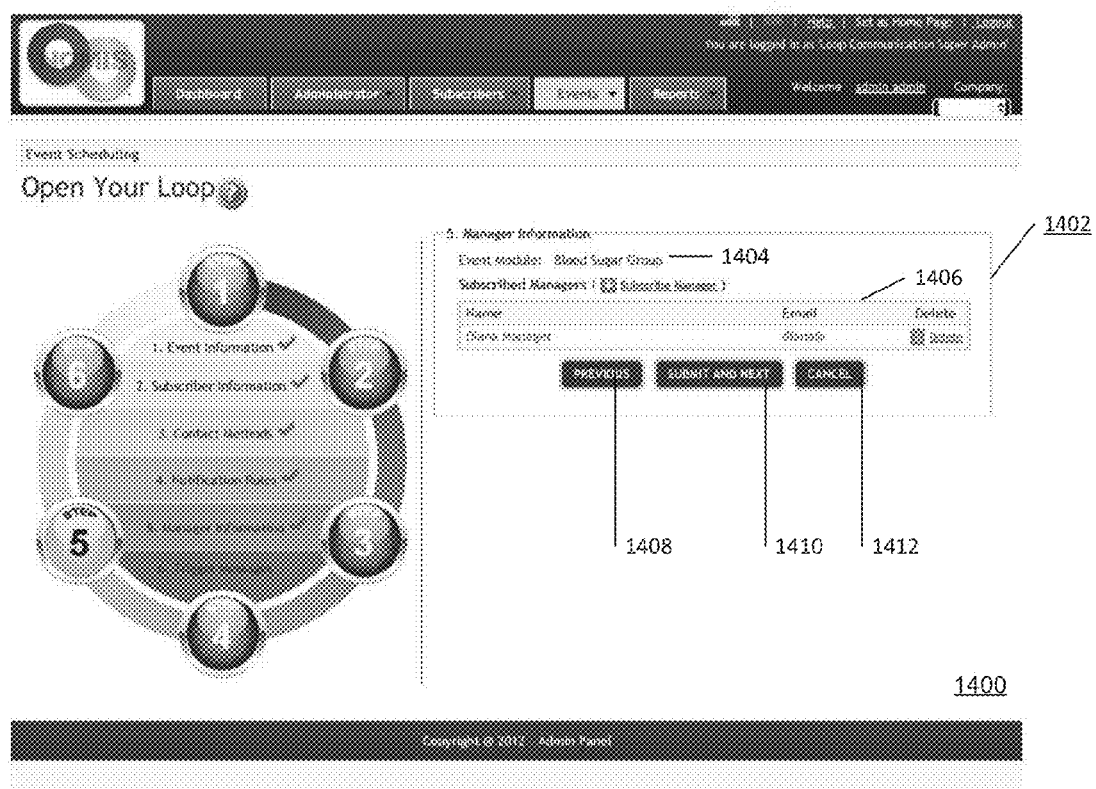
FIG. 14 is a screen shot of a manger information screen depicted in the process of FIG. 4.
Figure 15A:
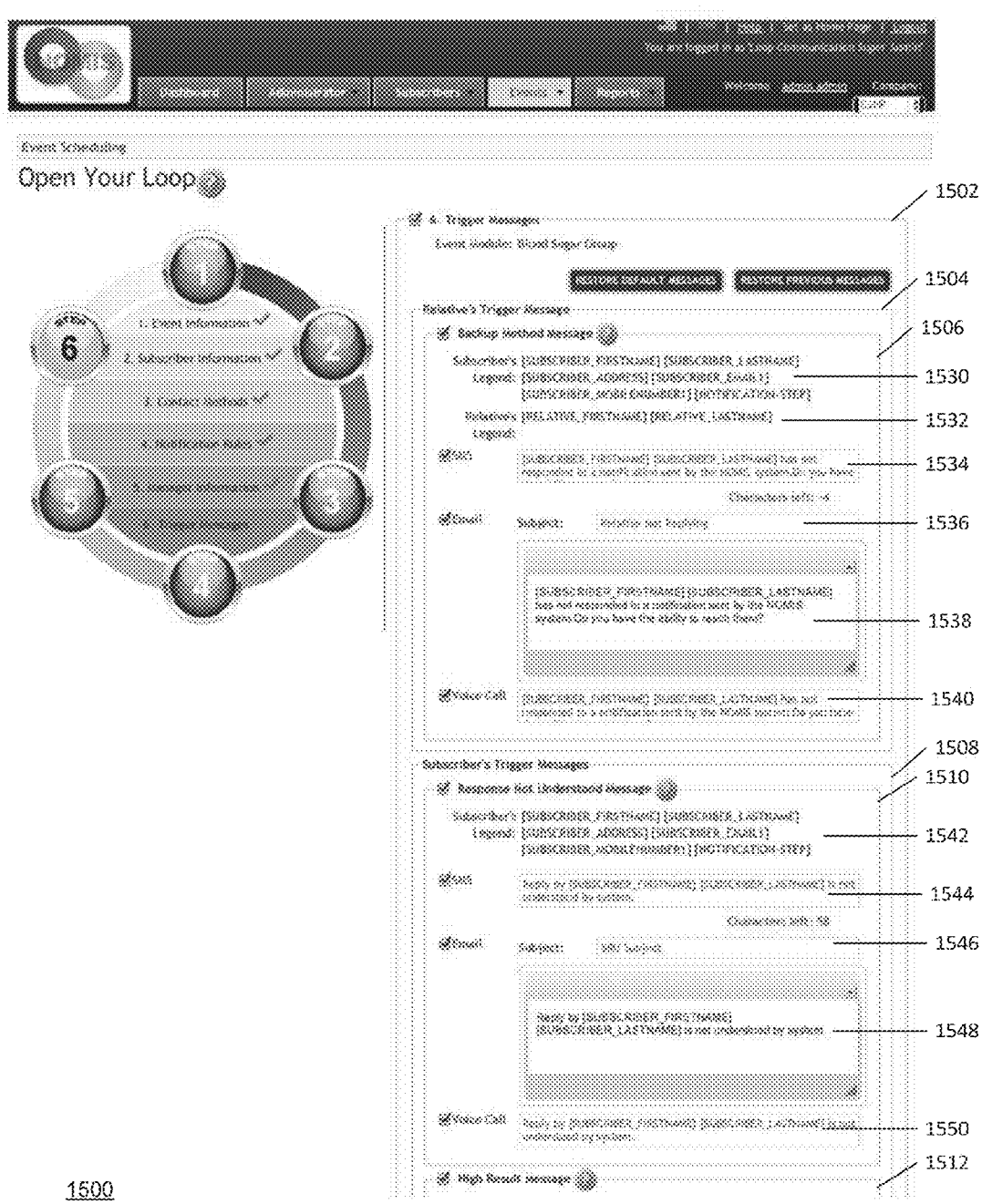
FIGS. 15A-15D is a screen shot of a trigger messages screen depicted in the process of FIG. 4.
Figure 15B:
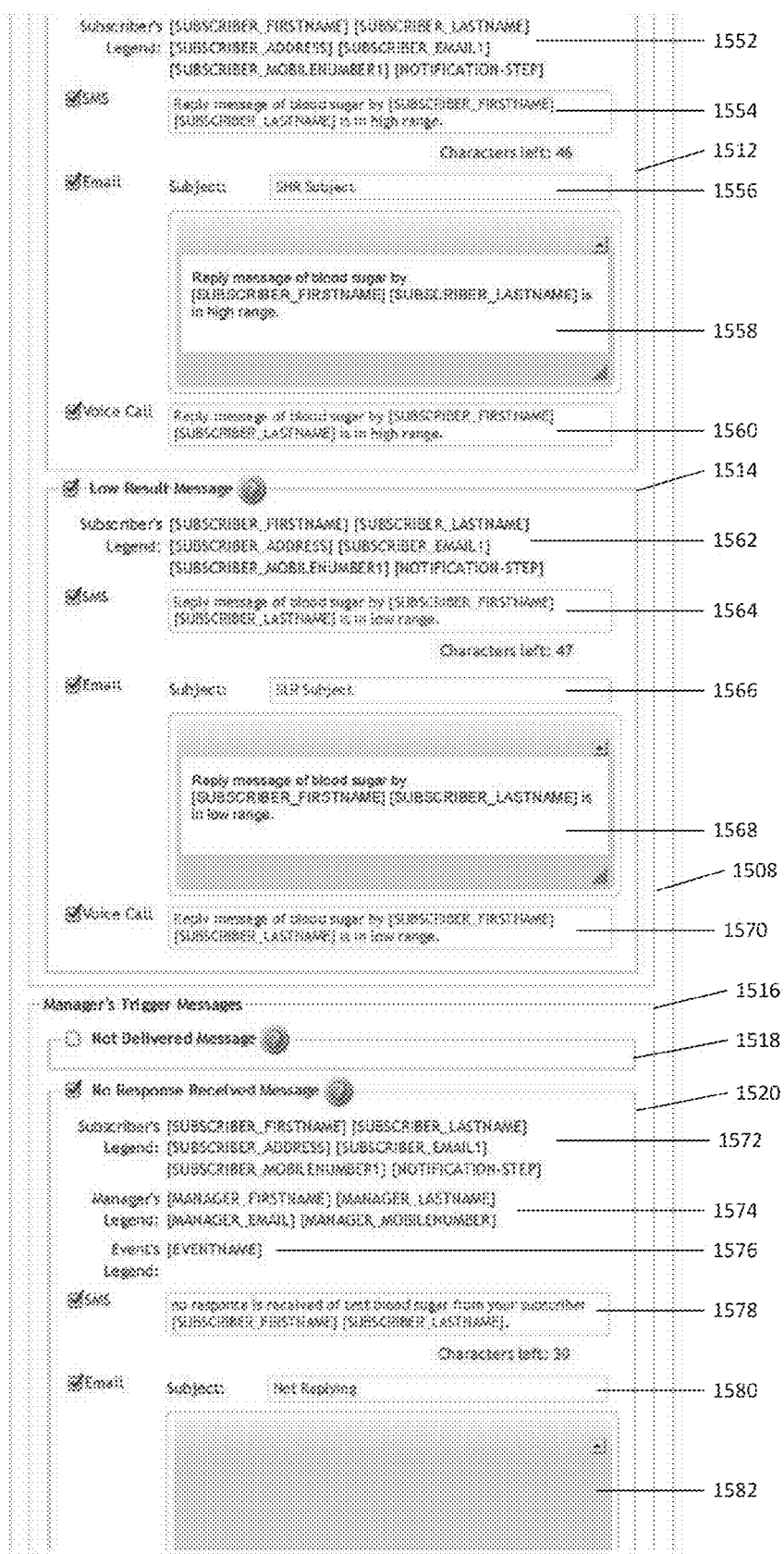
Figure 15C:
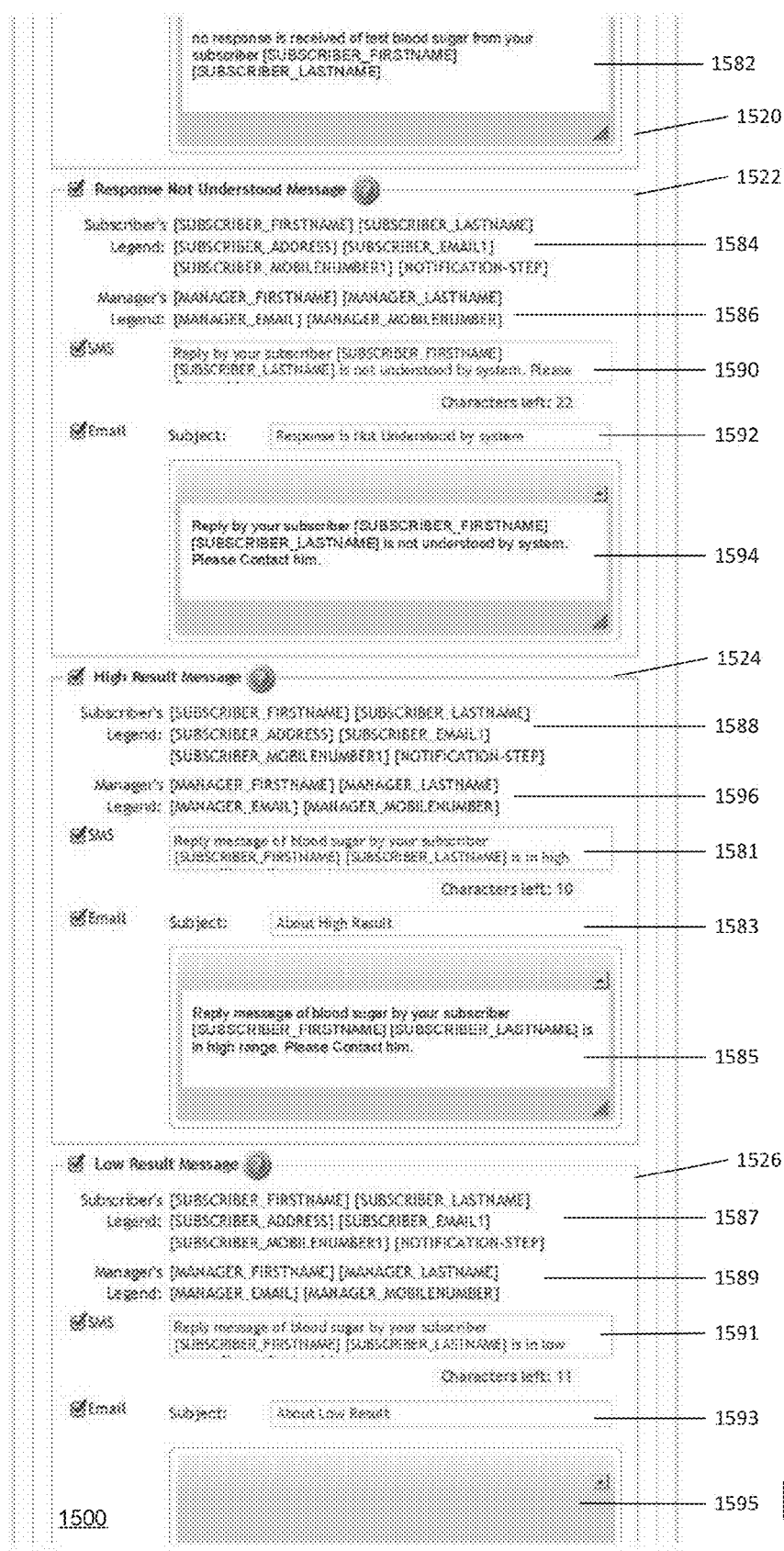
Figure 15D:
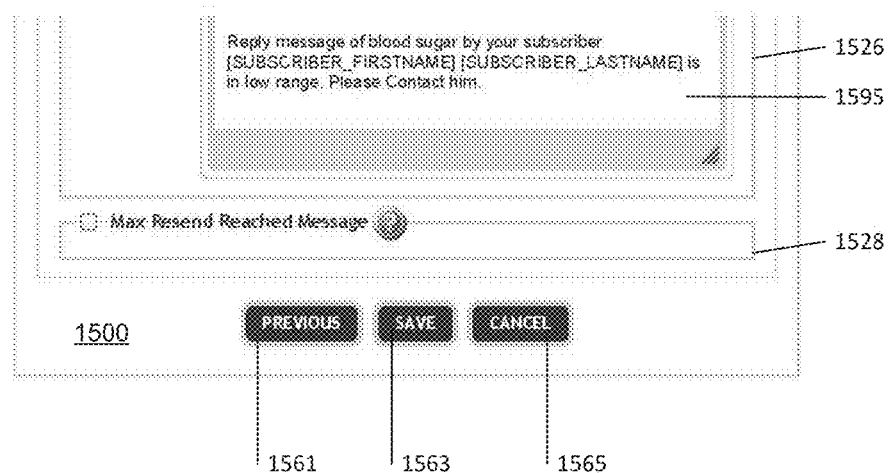

Referring now to FIG. 13, the event module has an event name display 1304 corresponding to the name of the event. A response required by subscriber field 1306 is configured to be used when a notification message from a subscriber/user is required. The resend notification before response module 1308 includes a resend time between notifications field 1316 configured to set a time before the next notification and a maximum number of iterations field 1318 configured to set the maximum number iterations of resend notifications.

The reply after response from subscriber module 1310 includes a plurality of resend message notification methods and resend message selection criteria similar to those as described with reference to FIG. 12.

More specifically, the resend notification messages may also be previously stored as the default message or messages previously used and loaded with the restore default messages command or restore previous messages command, respectively (not shown). The subscriber's legend field 1320 is configured to allow a user to merge fields listed in the text message field 1322. That is, in the text message field 1322 a user can create a customized notification message to be sent to a user utilizing message codes. For example, one illustrative message may include "Dear [[subscriber/user]] please respond with your drug/alcohol test results as soon as possible." Moreover, text field 1322 is associated with an SMS notification method or other text method.

Email notification field 1324 is a subject line for the resend email notification message and email resend notification field 1326 is a body of the message. Voice call resend notification field 1328 includes the body of the message to be utilized as text for the hearing impaired, text-to-voice or both. Other notification message modules may also be used, e.g., pictures, video and the like.

The response information module 1312 includes a plurality of selectable or fillable data fields configured to establish criteria for responses received. In this embodiment, the module 1312 includes a response type field 1330 as either numeric or text, a default value to response field 1332 and a low threshold value field 1334, normal range value field 1336 and high threshold value field 1338. These fields are utilized to set quantitative measure of predetermined criteria to close a communication loop.

In one embodiment, the fields are configured based on the subscribed end users needs. That is, a general Blood Pressure or Blood Glucose level legend can be used most of the time, however, not everyone is the same so the quantitative measurement will vary in what is normal, high, and low ranges in chronic disease patients. This area is specific to the healthcare modules of Blood Pressure and Blood Sugar. Therefore, the Blood Pressure module may be configured to choose [number of value to response: 2] creating two entry areas to account for 1—Systolic BP-highs, lows and normal range value and 2—Diastolic BP-highs, lows and normal range values, e.g., XXX/XXX data points corresponding to SBP/DBP. Also, with Blood Sugar, there would only be a need for one number value [number of value to response: 1] as shown in FIG. 13, e.g., XXX data point. Again, these fields are completely customizable to suit the user or subscribers needs.

The resend notification if not delivered module 1314 includes a resend time between notifications filed 1340 and a number of resends field 1342. These fields are utilized to specify time between notifications and number of resends. A resend response wait time after last notification field 1344 and voice call timeout field 1346 are utilized with the auto escalation method.

The user can select a previous command 1348 to return to the previous screen 1200, select a save command 1350 to save the notification rules on the server 102, select the submit and next command 1352 to save the notification rules on the server 102 and move to the next step, or select the cancel command 1354 to cancel this step and return to the dashboard 600.

After the user selects the submit and next command 1352 a manager information template 1400 is received on the user device. The manger information template 1400 includes a manager module 1402 having a plurality of selectable or fillable data fields for assigning specific managers for handling the events. In this embodiment, the manager information module 1402 includes an event module name field 1404 and a manager name field 1406 including at least one of name, email, phone number and other contact information.

The user can select a previous command 1408 command to return to the previous screen 1300, select a submit and next command 1410 to save the notification rules on the server 102 and move to the next step, or select the cancel command 1412 to cancel this step and return to the dashboard 600.

After the user selects the submit and next command 1410 a trigger messages information template 1500 is received on the user device. The trigger messages template 1500 includes a plurality of modules shown in FIGS. 15A-15D. The trigger messages module 1502 includes a plurality of modules including a relative's trigger message module 1504 including a backup method message module 1506. The trigger messages module 1502 also includes a subscriber's trigger messages module 1508 including a response not understood message module 1510, a high result message module 1512, and low result message module 1514. The trigger messages module 1502 also includes a manager's trigger messages module 1516 which includes a not deliver message module 1518, a no response received message module 1520, a response not understood message module 1522, a high result message module 1524, low result message module 1526 and max resend reached message module 1528.

The backup message module 1506 is configured to assign the backup notification method and message. In this embodiment, the backup method message module 1506 includes the backup notification messages, which may also be previously stored as default message or previous messages previously used and loaded with the restore default messages (not shown). The subscriber's legend field 1530 and relative's legend field 1532 is configured to allow a user to merge fields listed in the text message field 1534. That is, in the SMS message field 1534 a user can create a customized notification message to be sent to a user utilizing message codes of fields 1530 and 1532. For example, one illustrative message may include "Dear [[subscriber/user]] please respond with your physical therapy results as soon as possible." Moreover, text field 1534 is associated with an SMS notification method or other text method.

Email notification field 1536 is a subject line field for the trigger email notification message and email trigger notification field 1538 is a body of the message. Voice call trigger notification field 1540 includes the body of the message to be utilized as text for hearing impaired, text-to-voice or both. Other notification message modules may also be used, e.g., pictures, video and the like.

The subscriber's trigger messages module 1508 allows a user to provide criteria for trigger messages with regard to response not understood message module 1510, high result message module 1512, and low result message module 1514. The response not understood message module 1510 is configured to assign the return message and message notification method when the response is not understood. The module 1506 includes the response not understood notification messages, which may also be previously stored as default message or previous messages previously used and loaded with the restore default messages command or restore previous messages command, respectively (not shown). The subscriber's legend field 1542 is configured to allow a user to merge fields listed in the SMS message field 1544. That is, in the SMS message field 1544 a user can create a customized notification message to be sent to a user utilizing message codes of field 1542. For example, one illustrative message may include "Dear your response to your physical therapy result was not understood, please resend as soon as possible." Moreover, text field 1544 is associated with an SMS notification method or other text method.

The email notification field includes a subject line field 1546 for the response not understood message email notification message and email notification field 1548 is the body of the message. Voice call trigger notification field

1550 includes the body of the message to be utilized as text for hearing impaired, text-to-voice or both. Other notification message modules may also be used, e.g., pictures, video and the like.

The high result message module 1512 is configured to assign the return message and message notification method when a high result message is received from the user at the system. The module 1512 includes the high response messages and notification methods, which may also be previously stored as the default message or messages previously used and loaded with the restore default messages command or restore previous messages command, respectively (not shown). The subscriber's legend field 1552 is configured to allow a user to merge fields listed in the subscriber information template 704. That is, in the SMS message field 1554 a user can create a customized notification message to be sent to a user utilizing message codes of field 1552. For example, one illustrative message may include "Dear [[subscriber/user]] your response to your blood sugar message was in the high range." Moreover, text field 1554 is associated with an SMS notification method or other text method.

The email notification field includes a subject line field 1556 for the email notification message and email notification field 1558 is the body of the message to be sent. Voice call trigger notification field 1560 includes the body of the message to be utilized as text for hearing impaired, text-to-voice or both. Other notification message modules may also be used, e.g., pictures, video and the like.

The low result message module 1514 is configured to assign the return message and message notification method when a low result message is received from the user at the system. The module 1514 includes the high response messages and notification methods, which may also be previously stored as the default message or messages previously used and loaded with the restore default messages command or restore previous message command, respectively (not shown). The subscriber's legend field 1562 is configured to allow a user to merge fields listed in the SMS message field 1564. That is, in the SMS message field 1564 a user can create a customized notification message to be sent to a user utilizing message codes of field 1562. For example, one illustrative message may include "Dear [[subscriber/user]] your response to your blood sugar message was in the low range." Moreover, text field 1564 is associated with an SMS notification method or other text method.

The email notification field includes a subject line field 1566 for the email notification message and email notification field 1568 is the body of the message to be sent. The voice call trigger notification field 1570 includes the body of the message to be utilized as text for hearing impaired, text-to-voice or both. Other notification message modules may also be used, e.g., pictures, video and the like.

The manager's trigger messages module 1516 allows a manager to provide criteria for trigger messages with regard to a no response received module 1520, a response not understood message module 1522, a high result message module 1524, a low result message module 1526 and maximum resend module 1528. The no response received message 1520 is configured to assign the return message and message notification method when a response is not received. The module 1520 includes the response not understood notification messages, which may also be previously stored as the default message or messages previously used and loaded with the restore default messages command or restore previous messages command, respectively (not shown).

The subscriber's legend field 1572, manger's legend field 1574 and event's legend 1576 are configured to allow a user to merge fields listed in any template. For example, in the SMS message field 1578 a manager can create a customized notification message to be sent to a user utilizing message codes of fields of 1572, 1574, and/or 1576. For example, one illustrative message may include "Dear [[subscriber/user]] no response to your physical therapy result has been received, please send as soon as possible." Moreover, text field 1578 is associated with an SMS notification method or other text method.

The email notification field includes a subject line field 1580 for the response not understood message email notification message and email notification field 1582 is the body of the message. Other fields not shown, e.g., voice call trigger notification field may also be utilized along with other notification message modules, e.g., pictures, video and the like.

Message not understood message module 1522 is configured to assign the return message and message notification method when the response is not understood. The module 1522 includes the response not understood notification messages, which may also be previously stored as the default message or messages previously used and loaded with the restore default messages command or restore previous messages command, respectively (not shown). The subscriber's legend field 1584 and manger's legend field 1586 are configured to allow a user to merge fields from any template, e.g., subscriber data screen 700. That is, in the SMS message field 1590 a manger can create a customized notification message to be sent to a user. For example, one illustrative message may include "Dear [[subscriber/user]] your response to your blood sugar result was not understood, please resend as soon as possible." Moreover, text field 1590 is associated with an SMS notification method or other text method.

The email notification field includes a subject line field 1592 for the response not understood message email notification message and email notification field 1594 is the body of the message. Other notification message modules may also be used, e.g., voice, pictures, video and the like.

The high result message module 1524 is configured to assign the return message and message notification method when a high result message is received from the user at the system. The module 1524 includes the high response messages and notification methods, which may also be previously stored as the default message or messages previously used and loaded with the restore default messages command or restore previous messages command, respectively (not shown). The subscriber's legend field 1588 and Manager's legend field 1596 are configured to allow a manager to merge fields from any template listed in any message field. That is, in the SMS message field 1581 a manager can create a customized notification message to be sent to a user utilizing code from the legend. For example, one illustrative message may include "Dear [[subscriber/user]] your response to your blood sugar message was in the high range." Moreover, text field 1581 is associated with an SMS notification method or other text method.

The email notification field includes a subject line field 1583 for the email notification message and email notification field 1585 is the body of the message to be sent. Other notification message modules may also be used, e.g., voice, pictures, video and the like.

The low result message module 1526 is configured to assign the return message and message notification method when a low result message is received from the user at the system. The module 1526 includes the high response messages and notification methods, which may also be previously stored as the default message or messages previously used and loaded with the restore default messages command or restore previous messages command, respectively (not shown). The subscriber's legend field 1587 and manager's legend field 1589 are configured to allow a user to merge fields in any message. That is, in the SMS message field 1591 a user can create a customized notification message to be sent to a user utilizing with legend message codes. For example, one illustrative message may include "Dear [[subscriber/user]] your response to your blood sugar message was in the low range." Moreover, text field 1591 is associated with an SMS notification method or other text method.

The email notification field includes a subject line field 1593 for the email notification message and email notification field 1595 is the body of the message to be sent. Other notification message modules may also be used, e.g., voice, pictures, video and the like.

The user can select a previous command 1561 to return to the previous screen 1400, select the save command 1563 to save the notification rules on the server 102 and move to the next step 416 (in this case the next step is to start notifications, step 418), or select the cancel command 1565 to cancel this step and return to the dashboard 600.

Figure 16:
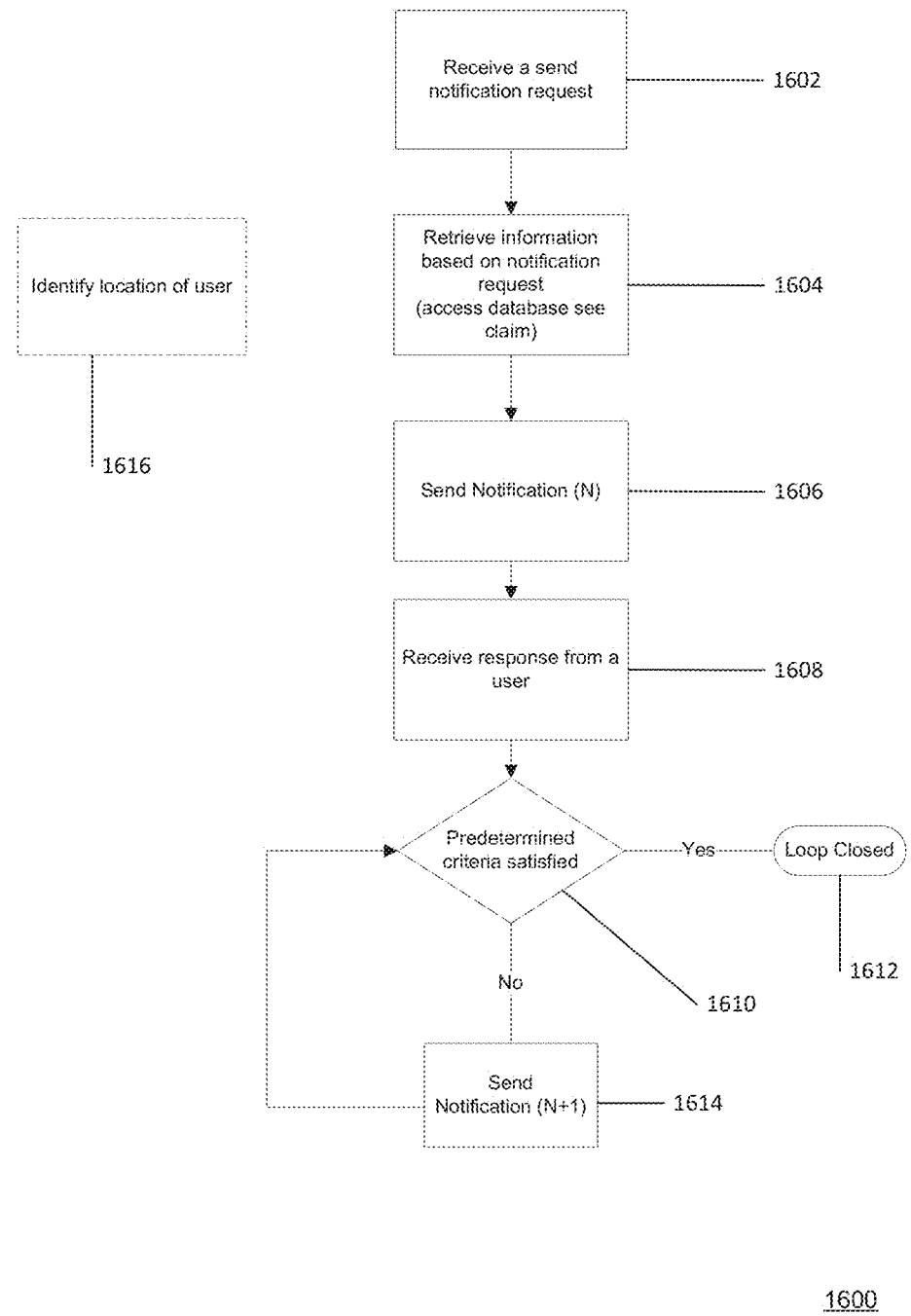
FIG. 16 is a block diagram of a user communication and notification and process according to an embodiment of the invention.

FIG. 16 is a block diagram of a user communication and notification process according to an embodiment of the invention.

Referring to FIG. 16, the communication and notification process are generally depicted as reference number 1600. After the registration process 1400 the system is active with the associated parameters. The system 100 receives a send notification request in step 1602 based on the registration parameters of process 1400. For example, based on the send notification request the system retrieves information 1604 saved in the process 1400 on the server 102, e.g., memory 156 and/or storage 158.

In this embodiment, the user information includes one or more user or subscriber profiles, notification message information including one or more notifications, notification method information including one or more notification methods, and predetermined criteria to close a communication loop. The information is previously described herein. In step 1606, a first notification (N) is sent to a user or subscriber based on one or more of the retrieved information is sent to user device 110 and/or subscriber device 112.

In step 1608, the system 100 receives a response from the user or subscriber. In preferred embodiment, the information is sent from user device 110 and/or subscriber device 112 over a network 104. In this embodiment, the user and the system 100 are at different locations. The system 100, e.g., processor 154 of the server 102, is configured to evaluate the first response to determine whether the response satisfies the predetermined criteria in step 1610. The predetermined criteria is established in process 400. In one embodiment, the predetermined criteria is established in the notification rules module 1302 with reference to FIG. 13. The criteria may include numerical value, response receipt, written text, voice, time, combinations of the same and others.

If the predetermined criteria has been satisfied in step 1610 the communication loop is closed, step 1612, and the overall record saved for use in a future report with the system 100. If the predetermined criteria has not been satisfied a second notification (N+1) 1614 is sent the user or subscriber and the process returns to step 1610. The second notification message and method of notification is established in the registration process 400, e.g., FIG. 13 above.

Optionally, the location of the user or subscriber in step 1616 may be established with techniques described herein. The location may sent to the system 100 and dynamically used in the notification (N) or (N+1). By way of illustrative example, the location of the user may be used to notify the user that they are close to testing facility for a drug and alcohol notification message.

Figure 17:
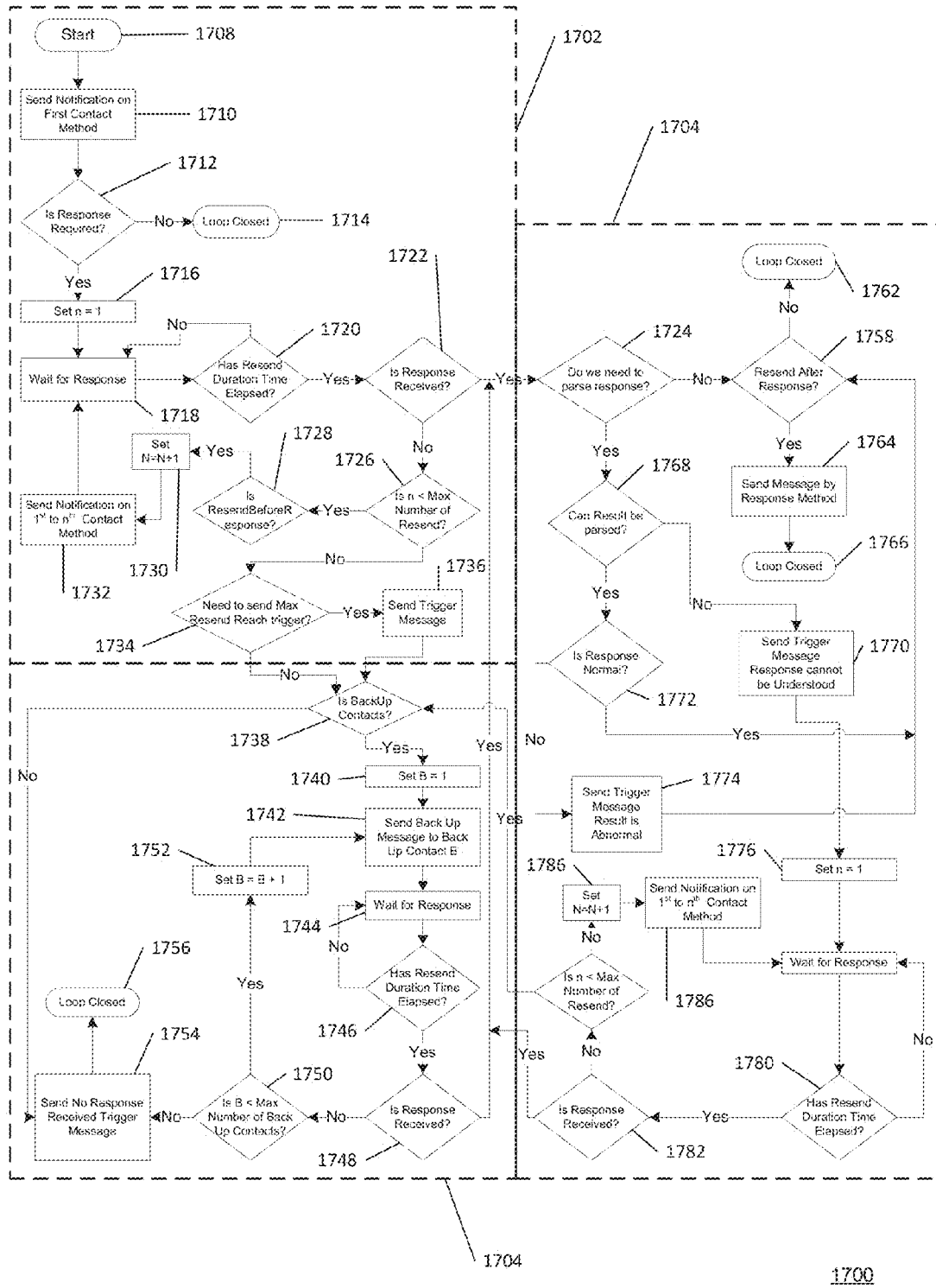
FIG. 17 is a block diagram of a user communication and notification and process according to an embodiment of the invention.

FIG. 17 is a block diagram of a user communication and notification process according to an embodiment of the invention.

Referring to FIG. 17, the communication and notification are generally depicted with reference to 1700. Generally, the process can be segregated into three global process modules including a notification module 1702, parsing and evaluating module 1704, and a backup module 1706.

The notification module 1702 is generally configured to send and receive notifications. The notification module 1702 includes a starting process step 1708, after a registration process as described herein, e.g., process 400. After starting the process 1708, the system 100 is configured to send a notification (N) with a first contact method (CM) specified in the registration process in step 1710. Whether a response is required is evaluated with the system 100, e.g., process or combination of other computational units of the server 102, step 1712. If a response is not required the communication loop is closed, step 1714. If a response is required step 1716 establishes the number of iterations (n) for the process in increments of one, e.g., set n=1. In step 1718, the system is configured to wait for a response for a predetermined duration as specified in the registration process. That is, the system 100 in step 1720 evaluates whether the resend duration time has elapsed. If the duration of time has not elapsed the system 100 loops back and continues to wait for a response in step 1718. If the resend duration of time has elapsed the system goes to step 1722.

In step 1722, the system 100 determines whether a response has been received. If a response has been received the system goes to the parsing and evaluating module 1704 via step 1724. If a response was not received the system goes to step 1726. In step 1726 the system evaluates whether the number of iterations (n) is less than the maximum number of resends ($R_{max}$). The maximum number of resends ($R_{max}$) is a predetermined number specified in the registration process 400. If the number of iterations is less than the maximum number of resends the system 100 goes to step 1728.

In step 1728 the system 100 determines whether the resend is before the response. That is, the system 100 evaluates whether the notification needs to be resent or whether a response has been received. If resend of the notification is required the system adjusts the notification message indicator from N to N+1, step 1730. Next in step 1732, a notification (second notification) is sent via the first contact method. Next the system returns to step 1718 waiting for the response as described herein.

Returning to step 1726, if the number of iterations is greater than the maximum number of resends the system 100 goes to step 1734. In step 1734 the system 100 is configured to evaluate whether a maximum trigger resend message has been established in the registration process 400. The maximum trigger resend message may be customized based on the history of the subscribed end user, a pre-determined number agreed upon by concerned parties. In one example, the maximum trigger resend messages could result in an automatic pre-scheduled 911 call. If the maximum trigger resend message has been established the system goes to step 1736 and sends the trigger message specified in the registration process 400. After the trigger message has been sent the system goes to the backup module 1706. If the maximum resend trigger has not been specified the system goes to the backup module 1706.

The backup module 1706 is configured to send and receive a plurality of notifications via the backup procedures specified in the registration process 400. More specifically, in step 1738 the system 100 evaluates whether there are backup contacts specified in the registration process 400. If there are backup contacts the system goes to step 1740. In step 1740 the system sets the backup contact (B) number to 1 and goes to set 1742. In step 1742, a first backup message is sent to the first backup contact with a first backup notification method. If there are no backups specified in the system 100 the system goes to step 1754 discussed below.

In step 1744, the system 100 is configured to wait for response for a predetermined duration specified in the registration process. That is, the system 100 in step 1746 evaluates whether the resend duration time has elapsed. If the duration of time has not elapsed the system 100 the system loops back and continues to wait for a response in step 1744. If the resend duration of time has elapsed the system 100 goes to step 1748.

In step 1748, the system 100 determines whether a response has been received. If a response has been received the system goes to the parsing and evaluating module 1704 via step 1724. If a response was not received the system goes to step 1750. In step 1750 the system evaluates whether the number of backup contacts (B) is less than the maximum number of backup contacts ($B_{max}$). The maximum number of backup contacts ($B_{max}$) is a predetermined number specified in the registration process 400. If the number of backup contacts is less than the maximum number of backup contacts ($B_{max}$) the system 100 goes to step 1752. In step 1752, the system 100 increments the backup contact by one, e.g., B+1, and returns to step 1742 to repeat the loop. If the number of backup contacts (B) is greater than the maximum number of backup contacts (Bmax) the system 100 goes to step 1754. In step 1754 the system 100, e.g., processor, sends a no response received trigger message previously specified in the system via the registration process 400. Next the system closes the backup loop in step 1756 and the record saved for use in a future report with the system 100.

The parsing and evaluating module 1704 is configured to parse and evaluate responses received with the system. More specifically, in step 1724 the system 100 determines whether the response needs to be parsed. That is, whether the receipt of the response is enough to satisfy the predetermined criteria of the system, e.g., something more than simply whether or not the response was received. For example, the system can be configured to understand the response by extracting information from the response, e.g., text, email, voice and the like. In one embodiment, the system is configured to extract a numerical value from the response, e.g., blood pressure, blood sugar, alcohol content, etc. If no parsing is required the system goes to step 1758. In step 1758 and the system determines whether a response is required to be sent to the user/subscriber's response. If no resend response is required to be sent the system goes to step 1762 and the communication loop is closed. If a resend response is required to be sent, e.g., a message such as "Please notify us when you have completed a drug test" then the system goes to step 1764 and sends the resend response by a resend response method. After that resend response has been sent the system goes to step 1766 and closes the communication loop.

Going back to step 1724, if a parse is required then the system goes to step 1768. In step 1768, the system 100 determines whether the result can be parsed, e.g., the result cannot be understood. If the result cannot be understood the system is configured to send a trigger message that the response cannot be understood in step 1770. If the result can be understood the system goes to step 1772 to determine whether the response is normal, e.g., within a predetermined range. Other criteria for determining whether the response is normal may include binary response criteria, greater than criteria, less than criteria, yes criteria, no critera, text responses consistent with the predetermined use of the system. If the system determines the response is normal the system goes to step 1758. If the system determines the response is abnormal it goes to step 1774. In step 1774 the system is configured in the registration process 400 to send a trigger message that result is abnormal and then returns to step 1758.

After step 1770 (sending a trigger message that the response can't be understood) the system goes to step 1776. In step 1776 the system sets the number of notifications for a response that cannot be understood $n_{nu}$ to one, $n_{nu}=1$ and goes to step 1778. In step 1778, the system 100 is configured to wait for response for a predetermined duration of time as specified in the registration process 400. That is, in step 1780 the system 100 evaluates whether the resend duration time has elapsed. If the duration of time has not elapsed the system 100 the system loops back and continues to wait for a response in step 1776. If the resend duration of time has elapsed the system 100 goes to step 1782.

In step 1782, the system 100 determines whether a response has been received. If a response has been received the system goes to the parsing and evaluating module 1704 via step 1724. If a response was not received the system goes to step 1784. In step 1784 the system evaluates whether the number of not understood messages $n_{nu}$ is less than the maximum number of not understood message ($n_{numax}$). The maximum number of not understood messages $n_{numax}$ is a predetermined number specified in the registration process 400. If the number of not understood messages nnu is less than the maximum number of not understood message ($n_{numax}$) the system 100 goes to step 1724. If the number of not understood messages $n_{nu}$ is greater than the maximum number of not understood message ($n_{numax}$) the system 100 goes to step 1786.

In step 1786, the system 100 increments the trigger message is abnormal by one, e.g., N+1, and returns to step 1788 to repeat the loop. In step 1788, the system sends a notification message via the contact method specified in the registration process and goes to step 1778. If the number of backup contacts (B) is greater than the maximum number of backup contacts ($B_{max}$) the system 100 goes to step 1754. In step 1754 the system 100, e.g., a processor, sends a no response received trigger message previously specified in the system to the user as specified in the registration process 400. Next the system closes the backup loop in step 1756.

Figure 18:
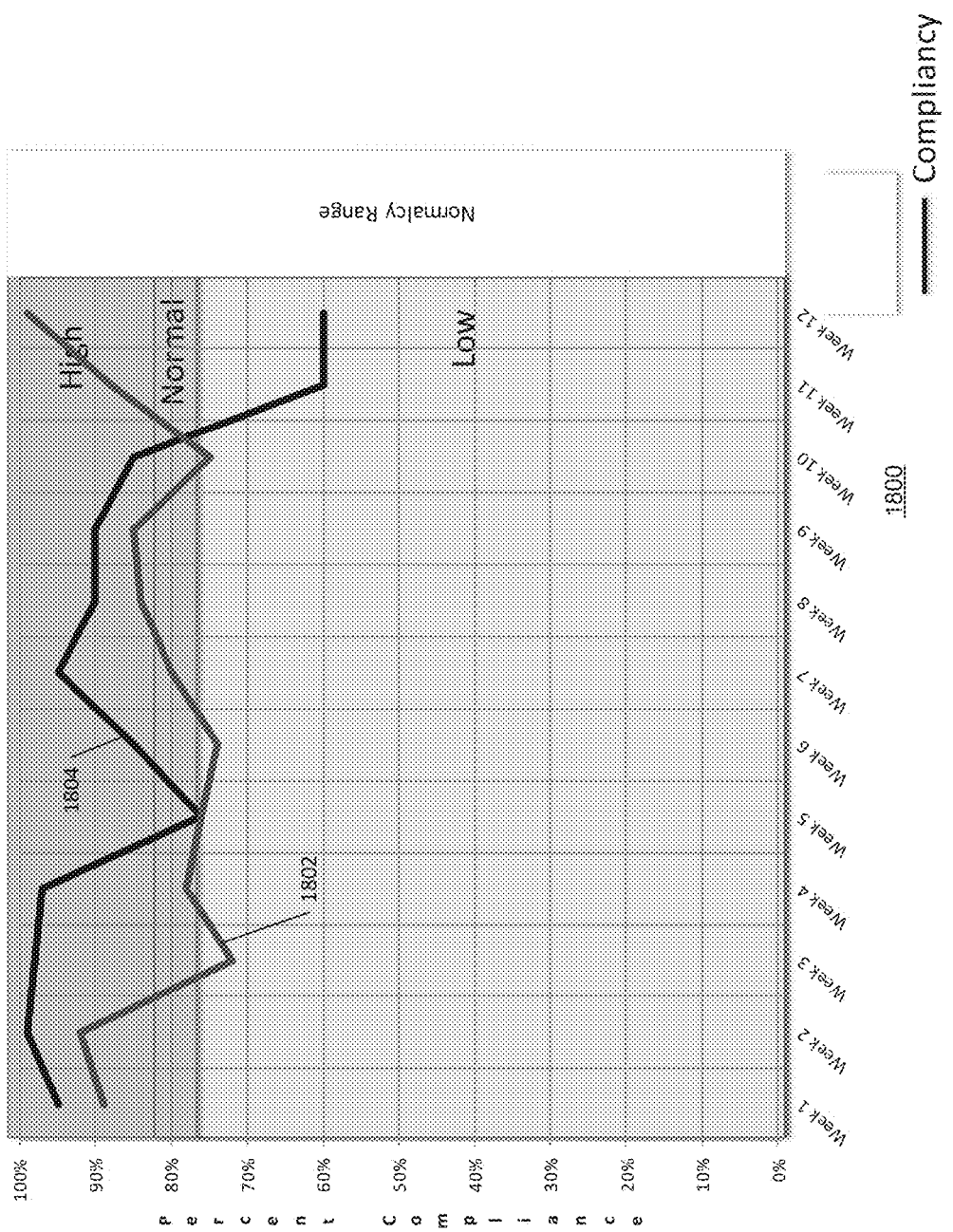
FIG. 18 is a screen shot of an output screen according to an embodiment of the invention.

FIG. 18 is a screen shot of an output screen according to an embodiment of the invention.

Referring to FIG. 18, the screen shoot is generally depicted as reference number 1800. The output 1800 includes a graphical output of the system specified in the registration process 400. Any number of different reports may be specified in the registration process. In this embodiment, the report 1800 includes data collected from twelve weeks of communications showing percent compliance on the y-axis and weeks on the x-axis. The output illustrates actual readings 1802 and compliance readings 1804.

Figure 19:
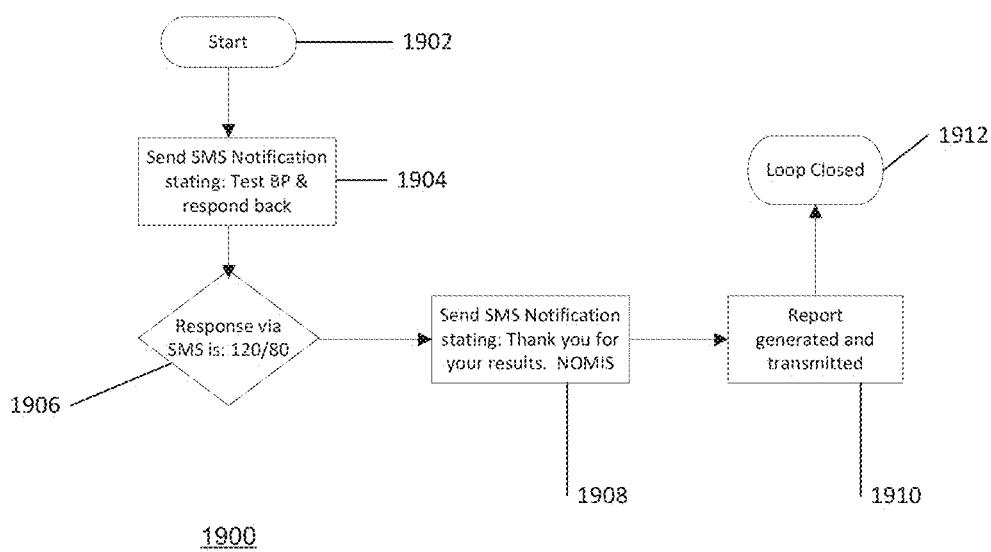
FIG. 19 is a block diagram of a user communication and notification process according to a blood pressure monitoring method with one device embodiment of the invention.

Referring to FIG. 19, the registration process 400 was completed for a user with one device and one notification method required to close the communication. The notification process is generally depicted as reference number 1900. The process starts after registration with step 1902. A first notification message stating, "Test blood pressure and respond back" was send via SMS to a user device in step 1904. A response 1906 was received via SMS communication over the network as 120/80. The system was configured to send a notification 1908 upon receipt of response from user stating, "Thank you for your results. NOMIS." In step 1910, the system was configured to generate and transmit a report to the subscriber and/or user and close the communication loop 1912. The subscriber in this embodiment could be a physician or insurance provider and the user could be a patient.

Figure 20:
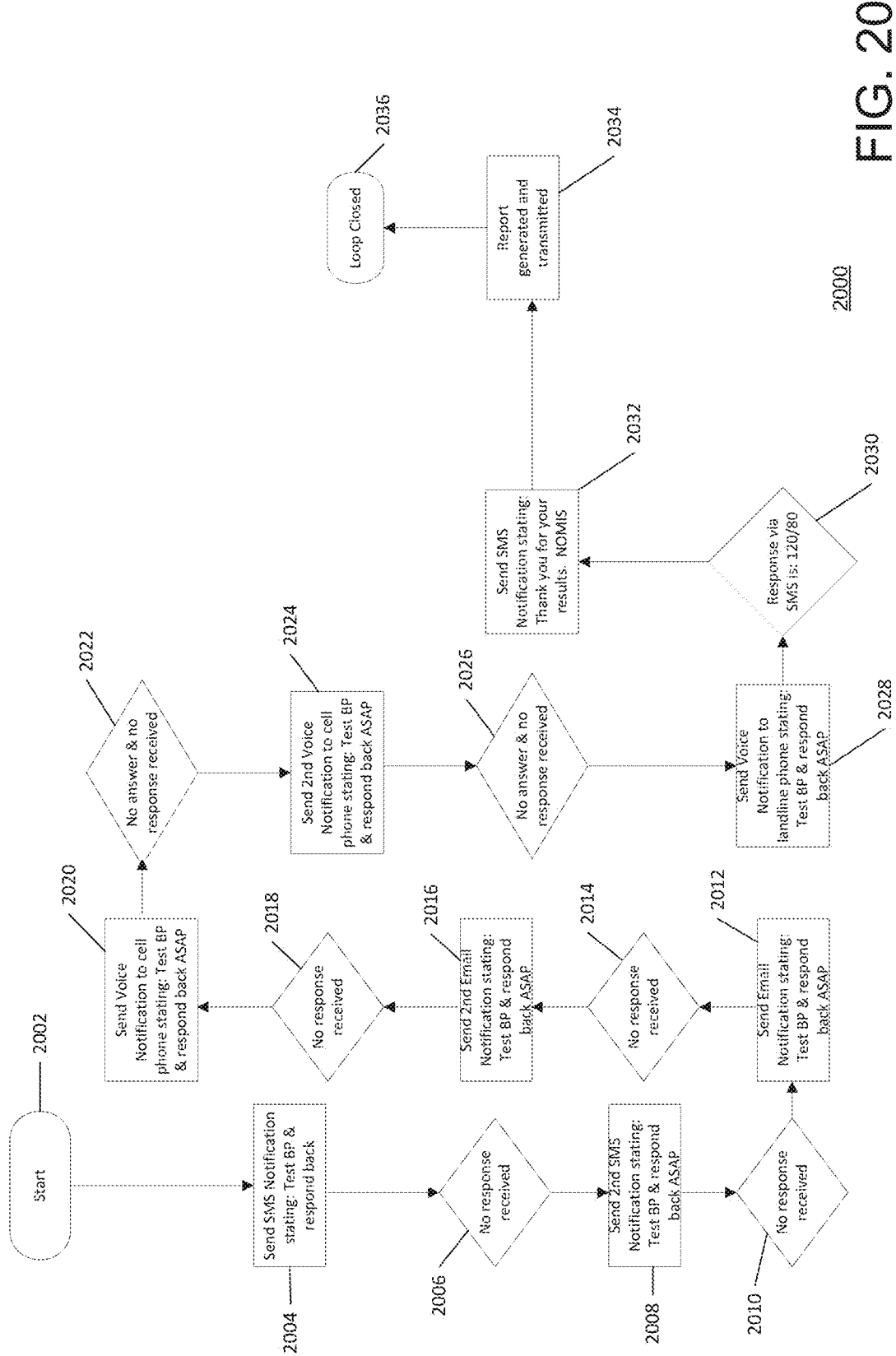
FIG. 20 is a block diagram of a user communication and notification and process according to a blood pressure monitoring method with more than one device embodiment of the invention.

FIG. 20 is a block diagram of a user communication and notification process according to a blood pressure monitoring method with a more than one device embodiment of the invention.

Referring to FIG. 20, the registration process 400 was completed for a user undergoing blood pressure monitoring with multiple devices and multiple notification methods required in order to close the communication loop or loops. The notification process is generally depicted as reference number 2000. The process starts after registration with step 2002. A first notification message stating, "Test blood pressure and respond back" was sent via SMS to a user device in step 2004. No response was received on the system 100, step 2006. A second SMS notification and a second notification method (same as the first notification and first notification method) was sent over the network, step 2008. No response was received to the second notification, step 2010.

A third notification with a third notification method was sent in step 2012. More specifically, an email notification was sent to the user device stating, "Test your blood pressure and respond back as soon as possible." In step 2014 the system determined that no response was received from the third notification. A fourth notification was sent with a fourth notification method in step 2016. The fourth notification was sent as an email stating, "Test your blood pressure and respond back as soon as possible." The system determined that no response was received from the fourth notification in step 2018.

In step 2020 a fifth notification message was sent with a fifth notification method. The fifth notification message was a voice notification and the notification was sent to a cell phone user device. The fifth notification stated, "Test blood pressure and respond back as soon as possible." Next in step 2022 the system 100 determined whether a response to any of the notifications including was received. It was determined in step 2022 no response was received. In step 2024 a sixth notification was sent with a sixth notification method. The sixth notification and sixth notification method was the same as the fifth notification and fifth notification method.

In step 2026 the system determined whether a response to any of the notifications was received. The system 100 determined that no response was received in step 2126 and goes to step 2128. In step 2028 a seventh notification with a seventh notification method was sent to the user. In this embodiment, the seventh notification is the same as the sixth notification, however, the seventh notification is sent to a landline device rather than to a cell phone, i.e., to a different user device. In step 2030 the system determined a response was received from the user via an SMS method received, the response stating, "120/80."

In step 2032 the system evaluated the response and determined an appropriate response to return based on rules in the registration process 400. In step 2032, the system 100 sent a response stating, "Thank you for your results. NOMIS." Optionally a report is generated, transmitted and stored in step 2034. The communication loop is now closed 2036.

Figure 21:
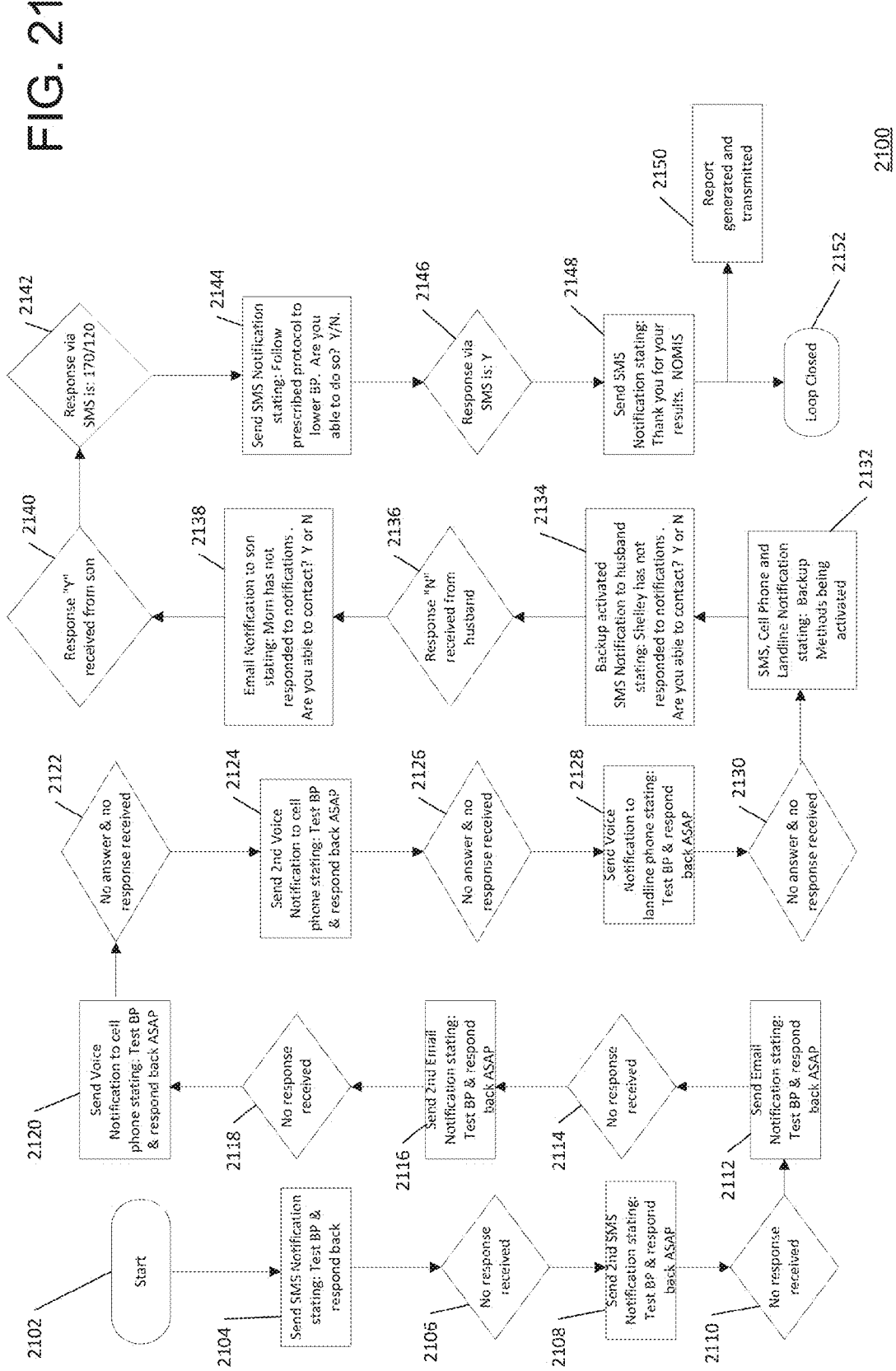
FIG. 21 is a block diagram of a user communication and notification process according to a blood pressure monitoring method with more than one device and backup notification embodiment of the invention.

FIG. 21 is a block diagram of a user communication and notification process according to a blood pressure monitoring method with more than one device and backup notification embodiment of the invention.

Referring to FIG. 21, the registration process 2100 was completed for a user undergoing blood pressure monitoring with multiple devices and backup methods required in order to close the communication loop or loops. The notification process is generally depicted as reference number 2100. The process starts after registration with step 2102. A first notification message stating, "Test blood pressure and respond back," was sent via SMS to a user device in step 2104. The system is configured to determine whether a response was received on the system 100, step 2106. In step 2106 it was determined that no response received. A second notification and a second notification method (same as the first method and first notification) was sent with SMS over the network, step 2108. The system is configured to determine whether a response was received to either notification in step 2110. It was determined that no response 2110 was received.

A third notification with a third notification method was sent in step 2112. More specifically, an email notification was sent to the user device stating, "Test your blood pressure and respond back as soon as possible." The system determined that no response was received from the third notification in step 2114. A fourth notification was sent with a fourth notification method in step 2116. The fourth notification was sent an email stating, "Test your blood pressure and respond back as soon as possible." The system determined that no response was received from the fourth notification in step 2118.

In step 2120 a fifth notification was sent with a fifth notification method. The fifth notification message was a voice notification and the notification was sent to a cell phone user device. The fifth notification stated, "Test blood pressure and respond back as soon as possible." Next in step 2122 the system 100 determined whether a response to any of the notifications including was received. It was determined in step 2122 that no response was received. In step 2124 a sixth notification was sent with a sixth notification method. The sixth notification and sixth notification method was the same as the fifth notification and fifth notification method.

In step 2126 the system determined whether a response to any of the notifications was received. The system 100 determined that no response was received in step 2126 and went to step 2128. In step 2128 a seventh notification with a seventh notification method was sent to the user. In this embodiment, the seventh notification is the same as the sixth notification, however, the seventh notification is sent to a landline device rather than to a cell phone, i.e., to a different user device. In step 2130 the system determined that no response was received.

In step 2132 an eight notification with an eighth notification message was sent to the user. The eighth notification stating, "No response has been received and backup methods are being activated." The eighth notification method includes a plurality of notification methods including a SMS method, cell phone method and landline method.

In step 2134 the system 100 sends a backup notification to a backup contact with a backup notification method. In this embodiment, the backup notification states, "Shelly has not responded to notifications. Are you able to contact Shelly?" The backup notification was sent via SMS method. In step 2136 the system determines whether a response to any of the notifications has been received. It was determined that a backup notification was received from the backup contact and that backup contact was not able to perform the action in the backup notification.

In step 2138 a second backup notification was sent to a second backup contact with a second backup notification method. In this embodiment, the second backup notification method was an email method, the second backup contact was to a son of the user and the second backup notification stated, "Mom has not responded to notifications are you able to contact?" In step 2140 the system determines whether a response to any of the notifications has been received. It was determined that a backup notification was received from the second backup contact and the response was a "Y." Moreover, a response from the user was received in step 2142 and the user response included, "170/120."

In step 2144 the system sends a trigger notification with a trigger notification message based on the result from step 2142. The trigger notification states, "Follow prescribed protocol to lower BP. Are you able to do so?" The trigger notification method is SMS method. In step 2146 the system receives a response of "Y" from the user and determines it was in response to the trigger notification and goes to step 2148. In step 2148 the system sends a message after response by a message after response method. The message after the response states, "Thank you for your results. NOMIS." Optionally a report is generated, transmitted and stored in step 2150. The communication loop is now closed 2152.

Figure 22:
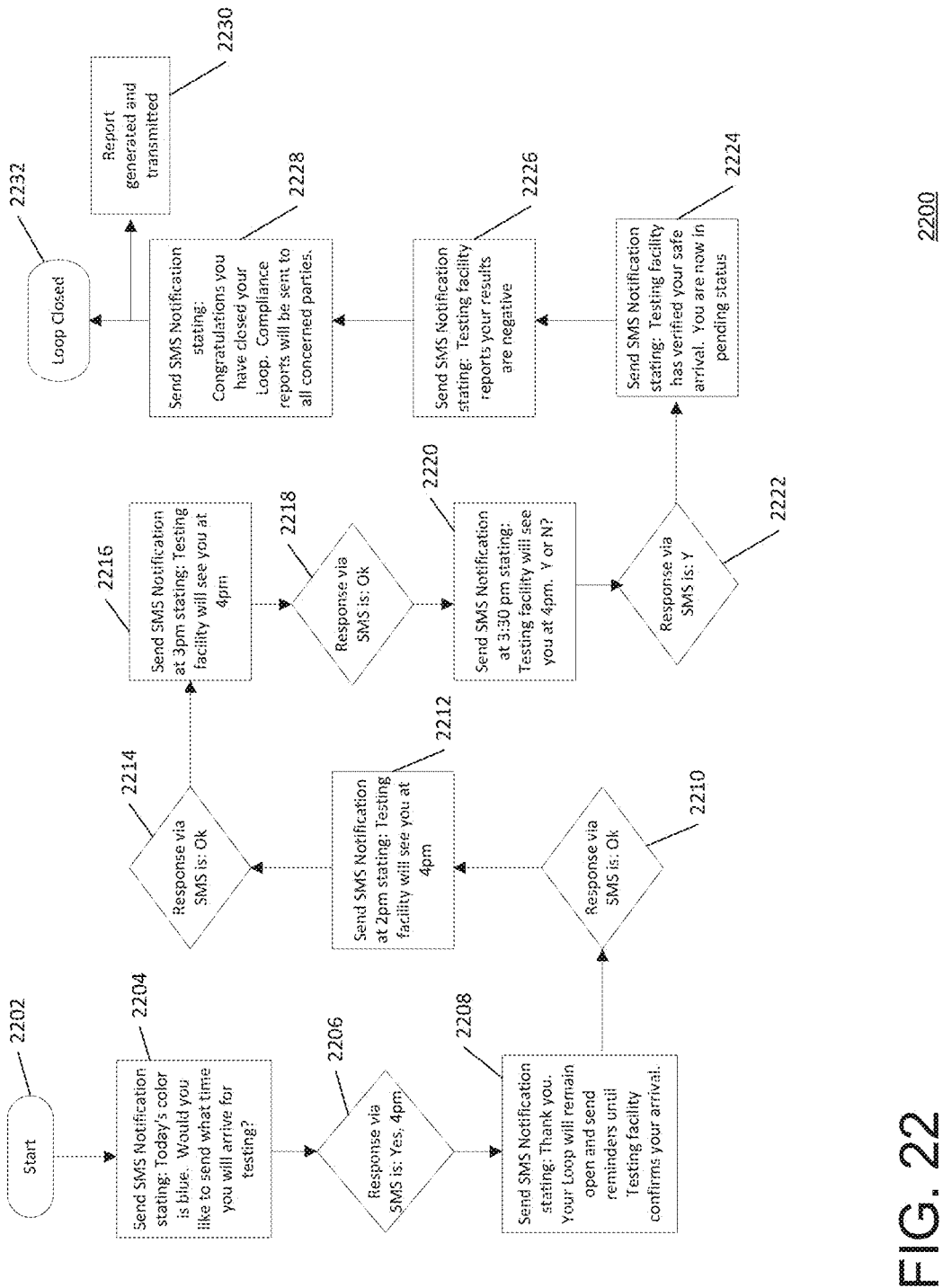
FIG. 22 is a block diagram of a user communication and notification process according to a random drug testing method with one device embodiment of the invention.

FIG. 22 is a block diagram of a user communication and notification process according to a random drug testing method with a one device embodiment of the invention.

Referring to FIG. 22 the process is generally depicted with reference to number 2200. This process is directed towards an embodiment where the user is required to submit to random drug tests and the system 100 has been registered with one device and one method necessary to close the communication loop. The process starts with in step 2202.

In step 2204 the system 100 sends a first notification with a first notification method. The first notification states, "Today's color is blue. Would you like to send what time you will arrive for testing?" The first notification method is an SMS notification method. The system in step 2206 waits for and receives a response stating, "Yes, 4 pm" for the user.

In step 2208 the system 100 sends a message after receipt of the response with a message after receipt of response method stating "Thank you. Your loop will remain open and we will send reminders until the testing facility confirms your test has been taken" The method for the message in step 2208 is an SMS notification. In step 2210, the system receives a response and determines an appropriate response to send with rules specified in the system 100 via the registration process 400. In step 2212 the system sends a notification stating, "The testing facility will see you at 4 pm," with the SMS method. In step 2214 the system 100 receives a response from the user stating, "Ok" via a SMS method.

In step 2216, the system receives a response and determines an appropriate response to send with rules specified in the system 100 via the registration process 400. In step 2216 the system sends a notification stating, "The testing facility will see you at 4 pm," with the SMS method. In step 2218 the system 100 receives a response from the user stating, "Ok" via a SMS method.

In step 2220, the system receives a response and determines an appropriate response to send with rules specified in the system 100 via the registration process 400. In step 2220 the system sends a notification stating, "The testing facility will see you at 4 pm. Y or N?" with an SMS method. In step 2222 the system 100 receives a response from the user stating, "Y" via SMS method.

In step 2224 the system sends a SMS notification stating, "The testing facility has verified your safe arrival. You are now in pending status." This communication was generated the system 100 based on communication received from the testing facility and rules specified in the registration process 400.

In step 2226 the system 100 sends a SMS notification stating, "The testing facility reports your results are negative." This communication was generated the system 100 based on communication received from the testing facility and rules specified in the registration process 400.

In step 2228 the system 100 sends a SMS notification stating, "Congratulations you have closed your loop. Compliance reports will be sent to all concerned parties." This communication was generated by the system 100 based on communication received from the testing facility and rules specified in the registration process 400. Optionally a report is generated, transmitted and stored in step 2230. The communication loop is now closed 2232.

Figure 23:
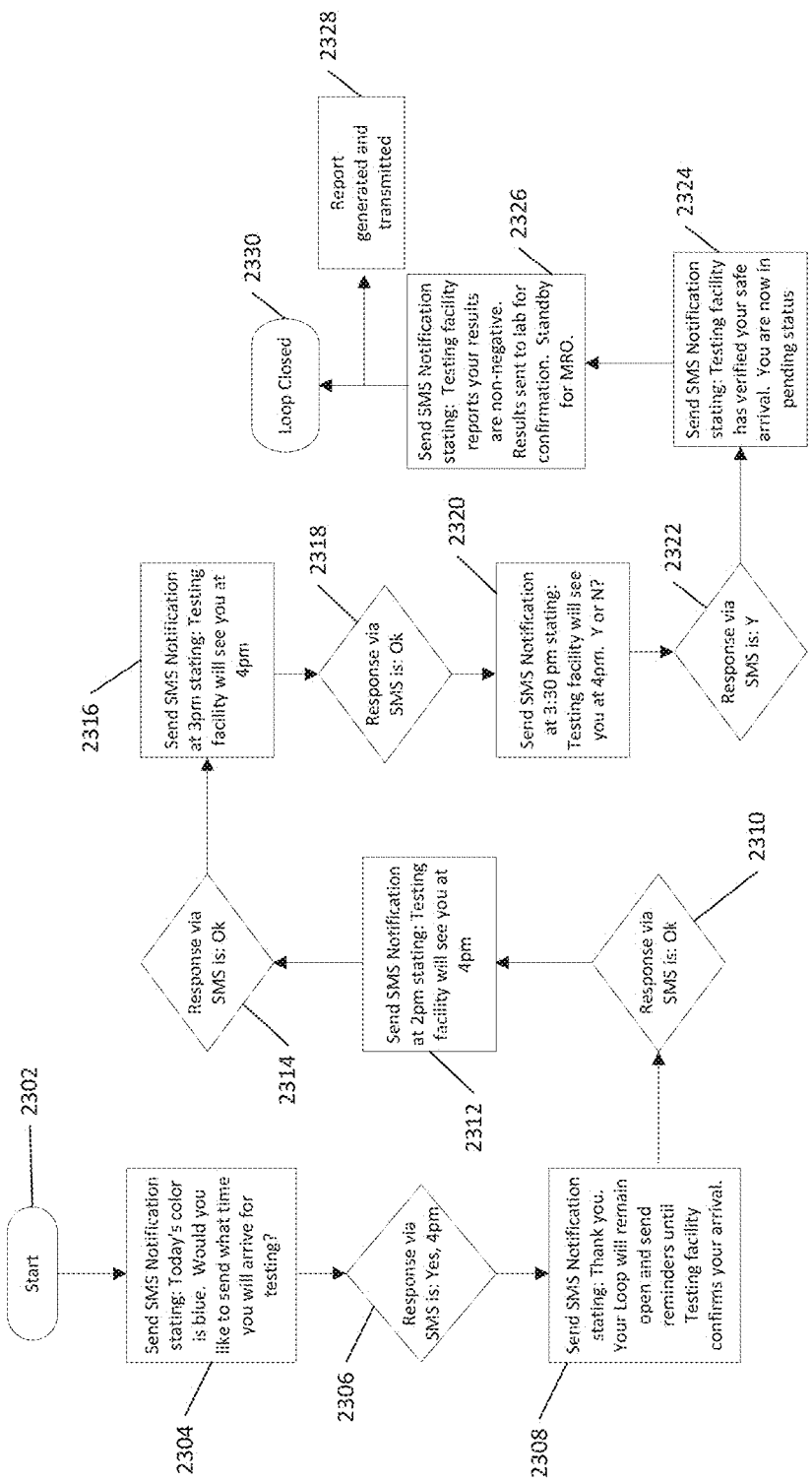
FIG. 23 is a block diagram of a user communication and notification process according to a random drug testing method with more than one device embodiment of the invention.

FIG. 23 is a block diagram of a user communication and notification process according to a random drug testing method with more than one device embodiment of the invention.

Referring to FIG. 23 the process is generally depicted with reference to number 2300. This process is directed towards an embodiment where the user is required to submit to random drug tests and the system 100 has been registered with one device and one method necessary to close the communication loop. The process starts with in step 2302.

In step 2304 the system 100 sends a first notification with a first notification method. The first notification states, "Today's color is blue. Would you like to send what time you will arrive for testing?" The first notification method is a SMS notification method. The system in step 2306 waits for and receives a response stating, "Yes, 4 pm," from the user.

In step 2308 the system 100 sends a message after receipt of the response with a message after receipt of response method stating "Thank you. Your loop will remain open and we will send you reminders until the testing facility confirms your test has been taken" The method for the message in step 2308 is a SMS notification. In step 2310, the system receives a response and determines an appropriate response to send with rules specified in the system 100 via the registration process 400. In step 2312 the system 100 sends a notification stating, "The testing facility will see you at 4 pm." with a SMS method. In step 2314 the system 100 receives a response from the user stating, "Ok" via a SMS method.

In step 2314, the system receives a response and determines an appropriate response to send with rules specified in the system 100 via the registration process 400. In step 2316 the system sends a notification stating, "The testing facility will see you at 4 pm," with the SMS method. In step 2318 the system 100 receives a response from the user stating, "Ok," via a SMS method.

In step 2318, the system receives a response and determines an appropriate response to send with rules specified in the system 100 via the registration process 400. In step 2320 the system sends a notification stating, "The testing facility will see you at 4 pm. Y or N?" with a SMS method. In step 2322 the system 100 receives a response from the user stating, "Y" via SMS method.

In step 2324 the system sends a SMS notification stating, "The testing facility has verified your safe arrival. You are now in pending status." This communication was generated by the system 100 based on communication received from the testing facility and rules specified in the registration process 400.

In step 2326 the system 100 sends a SMS notification stating, "The testing facility reports your results are non-negative. Results sent to lab for confirmation. Standby for MRO." This communication was generated by the system 100 based on communication received from the testing facility and rules specified in the registration process 400. Optionally a report is generated, transmitted and stored in step 2328. The communication loop is now closed 2330.

Figure 24:
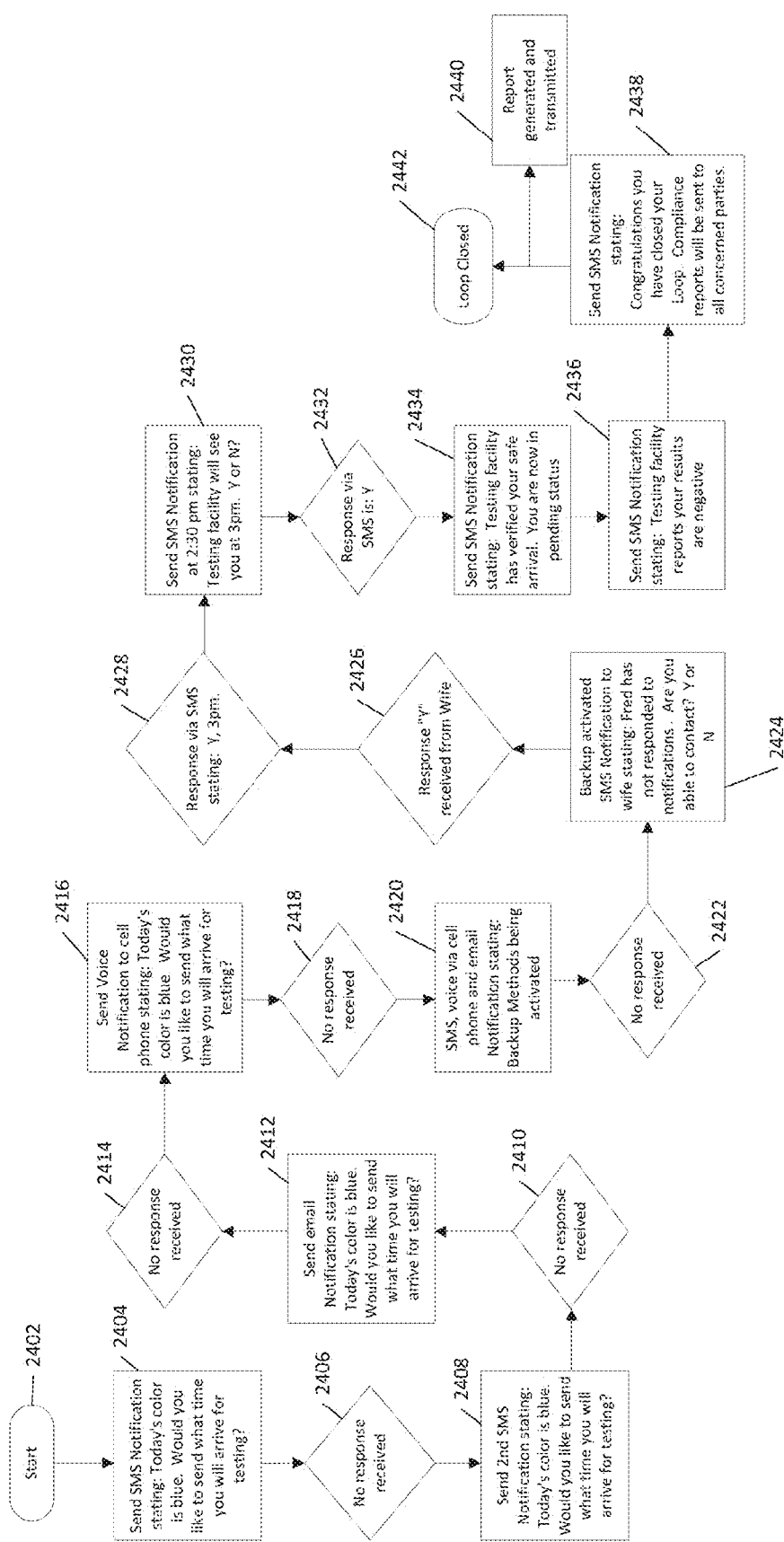
FIG. 24 is a block diagram of a user communication and notification process according to a random drug testing method with more than one device and backup method embodiment of the invention.

FIG. 24 is a block diagram of a user communication and notification process according to a random drug testing method with more than one device and backup method embodiment of the invention.

Referring to FIG. 24 the process is generally depicted with reference to number 2400. This process is directed towards an embodiment where the user is required to submit a random drug test and the system 100 has been registered with multiple devices and methods necessary to close the communication loop. The process starts with in step 2402.

In step 2404 the system 100 sends a first notification with a first notification method. The first notification states, "Today's color is blue. Would you like to send what time you will arrive time for testing?" The first notification method is a SMS notification method. The system in step 2406 waits for a response for a predetermined time established in the registration process 400 from the user—no response is received in step 2406.

In step 2408 the system 100 sends a second notification with a SMS method repeating the first notification. In step 2410, the system 100 waits for and receives no response to either notification from the user. In step 2412 the system 100 sends a third notification repeating the first notification message with an email notification method. In step 2414 the system 100 waits for a response for a predetermined amount of time established in the registration process 400 and receives no response from the user.

In step 2416 the system determines an appropriate notification to send with rules specified in the system 100 via the registration process 400. In this embodiment, the system 100 sends the same notification as the first notification, however, the system 100 sends the notification with a voice call to a user's cell phone. In step 2418 the system 100 waits for a predetermined amount of time specified in the registration process 400 and receives no response.

In step 2420, the system 100 determines an appropriate notification to send with rules specified in the system 100 via the registration process 400. In step 2420 the system sends a notification stating, "Backup methods are being activated." The system sends this backup notification with a plurality of different backup notification methods including SMS method, voice via cell phone method, and email method.

The system 100 performs another query for receipt of response from the user to any notification in step 2422. Step 2422 determines no responses have been received with the system 100. In step 2424 the system 100 sends a backup notification to a backup contact with a backup notification method. In this embodiment, the backup notification states "Fred has not responded to notifications. Are you able to contact Fred?" this backup notification was sent via SMS method. In step 2426 the system 100 determines whether a response to any of the notifications has been received. It was determined that a backup notification was received from the backup contact and that backup response was "yes." Moreover, a response from the user via SMS was received in step 2426 and the response stating "Y, 3 pm."

In step 2430, the system 100 determines an appropriate response to send with rules specified in the system 100 via the registration process 400 based on the response received in step 2428. In step 2430 the system sends a notification stating, "The testing facility will see you at 3 pm. Y or N?" with a SMS method. In step 2432 the system 100 receives a response from the user stating, "Y" via SMS method.

In step 2434 the system sends a SMS notification stating, "The testing facility has verified your safe arrival. You are now in pending status." This communication was generated by the system 100 based on communication received from the testing facility and rules specified in the registration process 400.

In step 2436 the system 100 sends a SMS notification stating, "The testing facility reports your results are negative." This communication was generated by the system 100 based on communication received from the testing facility and rules specified in the registration process 400.

In step 2438 the system 100 sends a SMS notification stating, "Congratulations you have closed your loop. Compliance reports will be sent to all concerned parties." This communication was generated by the system 100 based on communication received from the testing facility and rules specified in the registration process 400. Optionally a report is generated, transmitted and stored in step 2440. The communication loop is now closed 2442.

The inventions and methods described herein can be viewed as a whole, or as a number of separate inventions, that can be used independently or mixed and matched as desired. All inventions, steps, processed, devices, and methods described herein can be mixed and matched as desired. All previously described features, functions, or inventions described herein or by reference may be mixed and matched as desired. It will be apparent to those skilled in the art that various modifications and variations can be made in the present invention without departing from the spirit or scope of the invention. Thus, it is intended that the invention cover all of the modifications and variations of this invention provided they come within the scope of the appended claims and their equivalents.

What is claimed is:

1. A communication system for managing notifications and communications, comprising:
   a computing device comprising at least one processor and at least one memory, wherein the at least one processor and the at least one memory are communicatively arranged to:
   receive a send notification request at the communication system based on event information, the event information including information indicative of a start date of the event, a repeat frequency of the event, and an end date of the event;
   retrieve user information based on the send notification request, the user information including information indicative of: i.) a user or subscriber profile, ii.) a notification message information including one or more notifications, iii.) a notification method information including one or more notification methods, and iv.) a predetermined criteria to close a communication loop;
   send a first notification, based on the retrieved user information, wherein the first notification is sent with a first notification method, wherein a user and the communication system are at different locations;

receive a first response from the user in response to the first notification; and evaluate the first response to determine whether the first response satisfies the predetermined criteria and whether the first response needs to be parsed, when the first response satisfies the predetermined criteria close the communication loop and record the first response, when the first response does not satisfy the predetermined criteria send a second notification, when the first response needs to be parsed the system parses the first response to determine if the first parsed response can be understood, if the first parsed response can be understood determine whether the first parsed response satisfies the predetermined criteria, when the first parsed response satisfies the predetermined criteria close the communication loop and record the first parsed response, when the first parsed response does not satisfy the predetermined criteria send the second notification, and if the first parsed response cannot be understood send a notification having information indicative that the first response could not be understood, wherein the second notification is sent with a second notification method.

2. The communication system of claim 1, wherein the first notification method and second notification method comprises one or more of an email communication, an SMS communication, a landline voice call, a cell phone voice call, and a website notification.

3. The communication system of claim 1, wherein the first notification comprises a message requesting a user to perform a task.

4. The communication system of claim 1, wherein the predetermined criteria comprises subscriber defined criteria.

5. The communication system of claim 1, wherein the predetermined criteria comprises a numerical value.

6. The communication system of claim 1, further comprises the step of sending an output to a third party when the predetermined criteria has been satisfied.

7. The communication system of claim 6, wherein the third party comprises one or more of an employer, an insurance company, and a medical provider.

8. The communication system of claim 6, further comprising the steps of:
wait a predetermined duration for a second response; and
send a third notification, based on the user information, when the predetermined duration has elapsed, wherein the third notification is sent to a backup contact with a backup notification method, and wherein the backup contact is not the user.

9. A method for performing a notification service with a communication and notification system, comprising the steps of:
receiving a prescheduled send notification request based on event information at the communication and notification system, the event information including information indicative of a start date of the event, a repeat frequency of the event, and an end date of the event;
retrieving user information, at the communication and notification system based on the prescheduled send notification request received at the communication and notification system, the user information including: i.) one or more user profiles, ii.) a notification message information including one or more notifications, iii.) a notification method information including one or more notification methods, and iv.) a predetermined criteria to close a communication loop;
sending a first notification, with the communication and notification system, based on the user information, wherein the first notification is sent with a first notification method, wherein a user and the communication and notification system are at different locations;
receiving a first response, at the communication and notification system, from the user in response to the first notification; and
evaluating, with a processor, the first response to determine whether the first response satisfies the predetermined criteria and whether the first response needs to be parsed to understand the first response, when the first response needs to be parsed the communication and notification system parses the first response to determine if the first parsed response can be understood, if the first parsed response can be understood determine whether the first parsed response satisfies the predetermined criteria, when the predetermined criteria has been satisfied, close the communication loop and record the first response, when the first response has not been satisfied, send a second notification based on the user information, wherein the communication and notification system sends the second notification.

10. The method of claim 9, wherein the first notification method and second notification method comprise one or more of an email, an SMS communication, a landline voice call, a cell phone voice call communication, and a website notification.

11. The method of claim 9, wherein the first notification comprises a message requesting a user to perform a task.

12. The method of claim 11, wherein the predetermined criteria comprises information that is subscriber defined.

13. The method of claim 11, wherein the predetermined criteria comprises a numerical value.

14. The method of claim 11, further comprises the step of sending an output to a third party when the predetermined criteria has been satisfied.

15. A non-transitory computer-readable storage medium tangibly embodying a program of instructions executable by a machine wherein said program of instructions comprises a plurality of program codes for providing notifications and communications, said program of instructions comprising:
program code for receiving a send notification request based on event information, the event information including information indicative of a start date of the event, a repeat frequency of the event, and an end date of the event;
program code for retrieving user information based on the send notification request, the user information including information indicative of: i.) one or more user profiles, ii.) a notification message information including one or more notifications, iii.) a notification method information including one or more notification methods, and iv.) a predetermined criteria to close a communication loop;
program code for sending a first notification, based on the user information, wherein the first notification is sent with a first notification method, wherein a user and the computer-readable storage medium are at different locations;
program code for receiving a first response from the user in response to the first notification;
program code for evaluating the first response to determine whether the first response satisfies the predetermined criteria and whether the first response needs to be parsed to understand the first response, when the first response needs to be parsed the machine parses the first response to determine if the first parsed response can be understood, if the first parsed response can be understood determine whether the first parsed response satisfies the predetermined criteria, when the predetermined criteria has been satisfied close the communication loop and record the first response, when the first response has not been satisfied send a second notification, based on the user information, wherein the second notification is sent with a second notification method, the second notification includes a message that is different than the first notification and the second notification method is different than the first notification method;

program code for waiting a predetermined duration for a second response; and program code for sending a third notification, based on the user information, wherein the third notification is sent to a backup contact with a backup notification method, and wherein the backup contact is not the user.

16. The non-transitory computer-readable storage medium of claim 15, wherein the first notification method comprises one or more of an email, an SMS communication, a landline voice call, a cell phone voice call, and a website notification.

17. The non-transitory computer-readable storage medium of claim 16, wherein the first notification comprises a message requesting a user to perform a task.

18. The non-transitory computer-readable storage medium of claim 17, wherein the predetermined criteria comprises subscriber defined information.

\* \* \* \* \*